(12) United States Patent
Kiss

(10) Patent No.: US 7,790,685 B2
(45) Date of Patent: Sep. 7, 2010

(54) COMBINATIONS OF HUMAN PROTEINS TO ENHANCE VIABILITY OF TRANSPLANTED STEM CELLS AND PROGENITOR CELLS

(75) Inventor: Zoltan Kiss, Austin, MN (US)

(73) Assignee: Zoltan Laboratories LLC, Austin, TX (US)

( * ) Notice: Subject to any disclaimer, the term of this patent is extended or adjusted under 35 U.S.C. 154(b) by 0 days.

(21) Appl. No.: 12/189,446

(22) Filed: Aug. 11, 2008

(65) Prior Publication Data

US 2008/0299107 A1 Dec. 4, 2008

Related U.S. Application Data

(63) Continuation of application No. 11/560,167, filed on Nov. 15, 2006, now abandoned.

(60) Provisional application No. 60/804,060, filed on Jun. 6, 2006.

(51) Int. Cl.
*A61K 38/00* (2006.01)
*C07K 14/00* (2006.01)
*C07K 9/00* (2006.01)

(52) U.S. Cl. .................. 514/12; 435/183; 424/93.1; 424/94.6; 530/350

(58) Field of Classification Search .................. None
See application file for complete search history.

(56) References Cited

U.S. PATENT DOCUMENTS

| | | | |
|---|---|---|---|
| 5,405,772 A | 4/1995 | Ponting | |
| 7,374,754 B2 | 5/2008 | Kiss | |
| 7,544,509 B2 * | 6/2009 | Toma et al. | 435/325 |
| 2003/0158132 A1 * | 8/2003 | Kovesdi | 514/44 |
| 2005/0048046 A1 | 3/2005 | Kiss | |
| 2006/0128014 A1 | 6/2006 | Haggblad et al. | |
| 2007/0148140 A1 | 6/2007 | Kiss | |

FOREIGN PATENT DOCUMENTS

WO WO 2004/018655 3/2004

OTHER PUBLICATIONS

Cai et al., (NeuroMolecular Medicine, 2002, vol. 2, p. 233-249).*
Clarke et al. (2006), "Stem cells and cancer: Two faces of Eve," *Cell*, vol. 124, pp. 1111-1115.
Hong et al. (2005), "TAZ, a transcriptional modulator of mesenchymal stem cell differentiation," *Science*, 309, 1074-1078.
Herzog et al. (2003), "Plasticity of marrow-derived stem cells," *Blood*, 102, 3483-3493.
Seale et al. (2001), "The potential of muscle stem cells," *Developmental Cell*, 1, 333-342.
Ryan et al. (2005) "Mesenchymal stem cells avoid allogeneic rejection," *J. Inflammation*, 2:8, 1-11.
He et al. (2005), "Small intestinal organoid-derived SP cells contribute to repair of irradiation-induced skin injury," *Stem Cells Dev.*, 14, 285-291.

Millan et al. (1995), "Biology of human alkaline phosphatases with special reference to cancer," *Critical Reviews in Clinical Sciences*, 32, 1-39.
She et al. (2000), "Growth factor-like effects of placental alkaline phosphatase in human fetus and mouse embryo fibroblasts," *FEBS Letters*, 468, 163-167.
She et al. (2000), "Placental alkaline phosphatase, insulin, and adenine nucleotides or adenosine synergistically promote long-term survival of serum-starved mouse embryo and human fetus fibroblasts," *Cellular Signaling*, 12, 659-665.
Kozlenkov et al. (2002), "Function assignment to conserved residues in mammalian alkaline phosphatases," *J. Biol. Chem.*, 277, 22992-22999.
Beck et al. (1994), "Expression of human placental alkaline phosphatase in *Escherichia coli*," *Protein Expression and Purification*, 5, 192-197.
Heimo et al. (1998), "Human placenta alkaline phosphatase: Expression in *Pichia pastoris*, purification and characterization of the enzyme," *Protein Expression and Purification*, 12, 85-92.
Qian et al. (2002), "Targeted drug delivery via the transferrin receptor-mediated endocytosis pathway," *Pharmacol. Rev.*, 54, 561-587.
Carlevaro et al. (1997), "Transferrin promotes endothelial cell migration and invasion: Implication in cartilage neovascularization," *J. Cell. Biol.*, 136, 1375-1384.
Tomiya et al. (2003), "Complex -type biantennary *N*-glycans of recombinant human transferring from Trichoplusia ni cells expressing mammalian β-1,4-galactotransferase and β -1,4-*N*-acetylglucosaminenyltransferase II," *Glycobiology*, 13, 23-34.
Janciauskiene (2001), "Conformational properties of serine proteinase inhibitors (serpins) confer multiple pathophysiological roles," *Biochim. Biophys. Acta*, 1535, 221-235.
Finlay (1993), "$\alpha_1$-antitrypsin- and anchorage-independent growth of MCF-7 breast cancer cells," *Endocrinology*, 133, 996-1002.
Perraud et al. (1988),"Proliferation of rat astrocytes, but not of oligodendrocytes, is stimulated in vitro by protease inhibitors," *Int. J. Devl. Neuroscience*, 6, 261-266.
Dabbagh et al. (2001), "Alpha-1-antitrypsin stimulates fibroblast proliferation and procollagen production and activates classical MAP kinase signaling pathways," *J. Cell. Physiol.*, 186, 73-81.
Bergman et al. (1993), "Synthesis of $\alpha_1$-antichymotrypsin and $\alpha_1$-antitrypsin by human trophoblast," *Pediatric Res.*, 34, 312-317.
Leicht et al. (1982), "Sequence homology and structural comparison between the chromosomal human $\alpha_1$-antitrypsin and chicken ovalbumin genes," *Nature*, 297, 655-659.
Long et al. (1984), "Complete Sequence of the cDNA from human $\alpha_1$-antitrypsin and the gene for the S variant," *Biochemistry*, 23, 4828-4837.
Kwon et al. (1994), "Single amino acid substitutions of $\alpha_1$-antitrypsin that confer enhancement in thermal stability," *J. Biol. Chem.*, 269, 9627-9631.
Kataoka et al. (1999), "Enhanced tumor growth and invasiveness in vivo by a carboxyl-terminal fragment of $\alpha_1$-proteinase inhibitor generated by matrix metalloproteinases: A possible modulatory role in natural killer cytotoxicity," *American J. Pathol.*, 154, 457-468.

(Continued)

*Primary Examiner*—David S Romeo
*Assistant Examiner*—Daniel C Gamett
(74) *Attorney, Agent, or Firm*—Faegre & Benson LLP

(57) ABSTRACT

Embodiments of the present invention include the use of placental alkaline phosphatase alone or in combination with human transferrin and, optionally, human $\alpha_1$-antitrypsin to enhance the proliferation and survival of transplanted stem cells and stem cell-derived progenitor cells.

23 Claims, 2 Drawing Sheets

OTHER PUBLICATIONS

Bickford et al. (2006), "Nutraceuticals synergistically promote proliferation of human stem cells," *Stem Cells and Development*, 15, 118-123.

Chang et al. (1992), "Human placenta alkaline phosphatase: An improved purification procedure and kinetic studies," *Eur. J. Biochem.*, 209, 241-247.

Carmichael et al. (1987), "Evaluation of tetrazolium-based semiautomated colorimetric assay: Assessment of chemosensitivity testing," *Cancer Res.*, 47, 936-942.

Kimball et al. (1999), "Leucine regulates translation of specific mRNA in L6 myoblasts through mTOR-mediated changes in availability of eIF4E and phosphorylation of ribosomal protein S6," *J. Biol. Chem.*, 274, 11647-11652.

De Arcangelis et al. (2003), "IGF-I-induced differentiation of L6 myogenic cells requires the activity of cAMP-phosphodiesterase," *Mol. Biol. Cell*, 14, 1392-1404.

Guilherme et al. (2000), "Perinuclear localization and insulin responsiveness of GLUT4 requires cytoskeletal integrity in 3T3-L1 adipocytes," *J. Biol. Chem.*, 275, 38151-38159.

Pittenger et al. (1999), "Multilineage potential of adult human mesenchymal stem cells," *Science*, 284, 143-147.

Vas et al. (2005), "Biphasic effect of recombinant Galectin-1 on the growth and death of early hematopoietic cells," *Stem Cells*, 23, 279-287.

Kaeda et al. (2006), "Serial measurement of BCR-ABL transcripts in the peripheral blood after allogeneic stem cell transplantation for chronic myeloid leukemia: an attempt to define patients who may not require further therapy," *Blood*, 107, 4171-4176.

Jantunen et al. (2006), "Autologous stem cell transplantation in patients with chronic lymphocytic leukaemia: the Finnish experience," *Bone Marrow Transplantation*, 37, 1093-1098.

Woessmann et al. (2005), "Allogeneic haematopoietic stem cell transplantation in relapsed or refractory anaplastic large cell lymphoma of children and adolescents—a Berlin—Frankfurt—Münster group report," *British Journal of Haematology* 133, 176-182.

Bordignon (2006), "Stem-cell therapies for blood diseases," *Nature*, 441, 1100-1102.

Schneeweiss et al. (2001), "Comparison of Double and Triple High-Dose Chemotherapy with Autologous Blood Stem Cell Transplantation in Patients with Metastatic Breast Cancer," *Stem Cells* 19, 151-160.

Morley et al. (2001) Sarcopenia. *J. Lab. Clin. Med.* 137, 231-243.

van Leeuwen et al. (2003), "The embedded tumour: host physiology is important for the evaluation of tumour growth," Br. J. Cancer 89, 2254-2263.

Baracos (2001), "Management of muscle wasting in cancer-associated cachexia," Cancer 92, 1669-1677.

Chang et al. (1990), "Modification of human placental alkaline phosphatase by periodate-oxidized 1,$N^6$-ethenoadenosine monophosphate," Biochem. J,. 272, 683-690.

Doucet (2005), "Platelet Lysates Promote Mesenchymal Stem Cell Expansion: A Safety Substitute for Animal Serum in Cell-Based Therapy Applications," *Journal of Cellular Physiology*, 205, 228-236.

Zhang (2006), "Angiopoietin-like proteins stimulate ex vivo expansion of hematopoietic stem cells," *Nature Medicine*, 12:2, 240-245.

Koch (2005), "Insulin-like Growth Factor-I Induces Early Osteoblast Gene Expression in Human Mesenchymal Stem Cells," *Stem and Cells Development*, 14, 621-631.

She et al., "$\alpha$-1 antitrypsin can increase insulin-induced mitogenesis in various fibroblast and epithelial cell lines," FEBS Letters 473:33-36, 2000.

International Search Report and Written Opinion of international application No. PCT/US06/60956, mailed Dec. 19, 2007, 9 pp.

Beloti, Marcia Mateus et al., "Bone Cell Responses to the Composite of *Ricinus communis* Polyurethane and Alkaline Phosphatase", *Journal of Biomedical Materials Research*, vol. 84A, No. 2, Feb. 2008, pp. 436-441.

Filmon, R. et al., "Adherence of Osteoblast-like Cells on Calcospherites Developed on a Biomaterial Combining Poly(2-hydroxyethyl) Methacrylate and Alkaline Phosphatase", *Bone*, vol. 30, No. 1, Jan. 2002, pp. 115-158.

Hui, M. et al., "Stable Transfection of Nonosteogenic Cell Lines With Tissue Nonspecific Alkaline Phosphatase Enhances Mineral Deposition Both in the Presence and Absence of Beta-Glycerophosphate: Possible Role for Alkaline Phosphatase in Pathological Mineralization", *Calcified Tissue International*, vol. 60, No. 5, 1997, pp. 467-472.

Hui, Mi-Zhou et al., "Expression of Tissue Non-Specific Alkaline Phosphatase Stimulates Differentiated Behaviour in Specific Transformed Cell Populations", *The Anatomical Record*, vol. 244, No. 4, 1996, pp. 423-436.

Ulloa-Montoya, Fernando et al., "Culture Systems for Pluripotent Stem Cells", *Journal of Bioscience and Bioengineering*, vol. 100, No. 1, 2005, pp. 12-27.

Supplemental European Search Report issued in EP Application 06848420, published as 2 043 677, dated Jul. 31, 2009, 9 pages.

* cited by examiner

COMBINATIONS OF HUMAN PROTEINS TO ENHANCE VIABILITY OF TRANSPLANTED STEM CELLS AND PROGENITOR CELLS

CROSS REFERENCE TO RELATED APPLICATIONS

The present application is a continuation of U.S. patent application Ser. No. 11/560,167, titled "Combinations of Human Proteins to Enhance Viability of Stem Cells and Progenitor Cells" and filed Nov. 15, 2006, which claims the benefit of U.S. Provisional Application No. 60/804,060, titled "Combinations of Human Proteins to Enhance Viability of Stem Cells and Progenitor Cells" and filed Jun. 6, 2006. Both of these applications are incorporated herein by reference in their entirety.

FIELD OF THE INVENTION

This application provides a method using human placental alkaline phosphatase ("PALP") or other alkaline phosphatases alone or in combination with human transferrin (TF) and, optionally, human $\alpha_1$-antitrypsin (AT) to enhance survival and proliferation of transplanted pluripotent or multipotent stem cells and/or progenitor cells as well as more immediate precursors of differentiated cells.

BACKGROUND

Replacement of mature cells in any living tissue involves a highly regulated process in which a small population of long-lived self-renewing adult stem cells gives rise to relatively short-lived proliferating progenitor cells, also called transit-amplifying cells. Progenitor cells undergo limited number of mitotic division with each successive daughter cell population expressing increasing degree of differentiation and a decreased capacity to proliferate. Eventually this process leads to the formation of fully differentiated cells that lose their ability to differentiate [Clarke, M. F. and Fuller, M. (2006), "Stem cells and cancer: Two faces of Eve," Cell, 124, 1111-1115]. This process ensures production of large numbers of differentiated progeny from a small number of stem cells. Nature appears to have developed such mechanism for tissue renewal to decrease the risk of cancer. Limiting the number of cells with high proliferative capacity limits the risk of developing cancer that is proportional to the number of cell proliferative events [Clarke, M. F. and Fuller, M. (2006), "Stem cells and cancer: Two faces of Eve," Cell, 124, 1111-1115].

Various transcription factors play key roles in the differentiation of stem cells. For example, the Runx2 and PPARγ transcription factors along with the TAZ transcriptional modulator drive mesenchymal stem cells to differentiate into either osteoblasts or adipocytes [Hong, J. H., Hwang, E. S., McManus, M. T., Amsterdam, A., Tian, Y., Kalmukova, R., Mueller, E., Benjamin, T., Spiegelman, B. M., Sharp, P. A., Hopkins, N. and Yaffe, M. B. (2005), "TAZ, a transcriptional modulator of mesenchymal stem cell differentiation," Science, 309, 1074-1078]. Appropriately selective modulation of these transcription factors and other regulators will determine which cell type these stem cells will differentiate into.

In addition to replacing dying cells as part of a normal physiological process, there are also many pathological situations when regeneration of a tissue is necessary to regain normal function. Pluripotent or multipotent embryonic and adult stem cells as well as progenitor cells hold great promise to help tissue regeneration. For example, hematopoietic stem cells have the capacity to reconstitute the entire hematopoietic system of a myeloblated host [Herzog, E. L., Chai, L. and Krause, D. S. (2003), "Plasticity of marrow-derived stem cells," Blood, 102, 3483-3493]. Bone marrow-derived mesenchymal stem cells can also differentiate ex vivo and in vivo into multiple cell lineages including chondrocytes, osteoblasts, epithelial cells, myocytes, fibroblasts, keratinocytes, adipocytes, pneumocytes and early neural precursors. Thus, mesenchymal stem cells have the potential to replace damaged cells with normally functioning cells in tissues such as the cartilage, skeletal and heart muscle, bone, tendon, kidney, gastrointestinal tract, liver, ligament, skin, nervous system, and adipose tissue [Seale, P., Asakura, A. and Rudnicki, M. A. (2001), "The potential of muscle stem cells," Developmental Cell, 1, 333-342; Ryan, J. M., Barry, F. P., Murphy, J. M. and Mahon, B. P. (2005), "Mesenchymal stem cells avoid allogeneic rejection," J. Inflammation, 2:8, 1-11; Herzog, E. L., Chai, L. and Krause, D. S. (2003), "Plasticity of marrow-derived stem cells," Blood, 102, 3483-3493].

SUMMARY OF THE INVENTION

One embodiment of the invention is directed toward a method for stimulating proliferation and promoting survival of stem cells by administering a composition that includes alkaline phosphatase or an active derivative thereof or a combination of alkaline phosphatase and transferrin and optionally $\alpha_1$-antitrypsin and derivatives thereof In some embodiments the alkaline phosphatase used is placental alkaline phosphatase. In other embodiments, the stem cells include adult stem cells, embryonic stem cells or progenitor cells.

DETAILED DESCRIPTION

Figure 1:
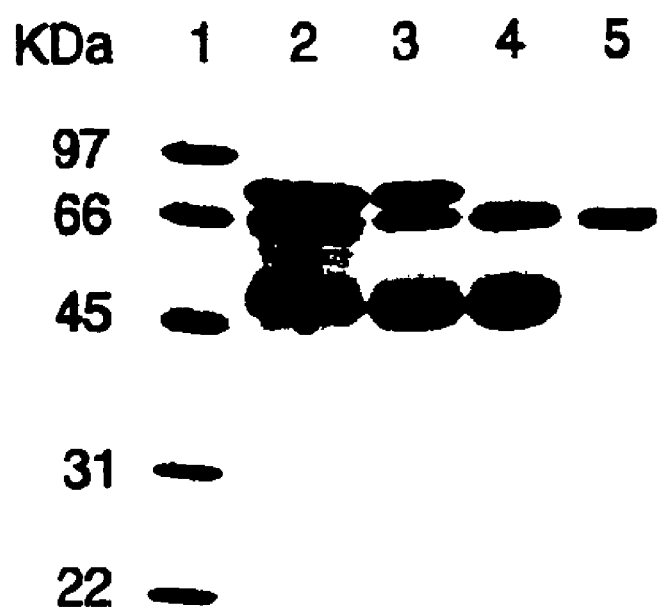
FIG. 1 shows a digital image of a gel separation, demonstrating that the PALP used for the experiments, except when indicated otherwise, was homogeneous or near homogeneous. The image also shows the protein composition of the starting commercial PALP preparation, the three major bands being represented by TF alone (80 kDa), a mixture of albumin and PALP (~66-68 kDa) at a ratio of approximately 3:1, and AT (52 kDa).

Stem cell-derived progenitor cells, particularly the more immediate precursors of differentiated cells, have narrower range of possibilities to differentiate, i.e. they are more committed to a certain cell lineage. Even though serial cell division leads to proliferating progenitor cell populations that increasingly express markers of differentiation, in an embodiment of the invention all progenitor cell populations that are capable of mitosis are considered to be progenitor cells and are within the scope of this present application. For example, proliferating myoblasts and pre-adipocytes, including those presented in the Examples, are covered by embodiments in this invention as progenitors.

An embodiment of the invention also includes certain stem cell-like cells or committed stem cells such as satellite cells in the muscle. Satellite cells were previously considered to be unipotent, since they yield mostly myogenic precursor cells (myoblasts). However, recent studies suggest that satellite cells may exist as a more heterogeneous population with different subpopulations exhibiting distinct properties [Seale, P., Asakura, A. and Rudnicki, M. A. (2001), "The potential of muscle stem cells," *Developmental Cell*, 1, 333-342]. It has also been recognized that isolated stem cells are composed of subpopulations with slightly different characteristics. For example, "side population" cells are believed to be a subpopulation of stem cells characterized by their ability to efflux the fluorescent dye Hoechts 33342 [He, D. N., Qin, H., Liao, L., Li, N., Zhu, W. M., Yu, B. J., Wu, X., Zhao, R. C. and Li, J. S. (2005), "Small intestinal organoid-derived SP cells contribute to repair of irradiation-induced skin injury," *Stem Cells Dev.*, 14, 285-291]. Because the relatively small differences among various subpopulations do not alter the basic characteristics of a stem cell, in the application, the term "stem cell" covers all pluripotent/multipotent subpopulations of stem cells or "side population" cells as well as embryonic and adult stem cells regardless of the origin of the tissue.

An embodiment of the present invention includes the use of placental alkaline phosphatase ("PALP") and other members of the alkaline phosphatase family with or without transferrin (TF) and, optionally, $\alpha_1$-antitrypsin (AT) to enhance proliferation and survival of adult or embryonic stem cells as well as stem cell-derived progenitor cells including more immediate proliferating precursors of differentiated cells such as myoblasts and pre-adipocytes. Alkaline phosphatase and the other proteins in some embodiments of this invention can be used in vitro to maintain viability and expand the number of stem/progenitor cells. These proteins can also be used in vivo to enhance the efficacy of the transplantation process, including transplantation of bone marrow or bone marrow-derived mesenchymal stromal or hematopoietic stem/progenitor cells, by enhancing the survival and proliferation of transplanted stem cells or progenitor cells. Finally, these proteins can be used to promote survival and stimulate proliferation of endogenous tissue-specific or bone marrow-derived stem cells and non-differentiated progenitor cells thereby facilitating re-population of damaged tissue with healthy differentiated cells. PALP may be used alone or in combination with TF and, optionally, AT to restore the normal function of the affected diseased tissue by promoting the survival and proliferation of the transplanted and/or endogenous stem cells or progenitor cells.

One advantage of using PALP, TF and, in some cases, AT for stem/progenitor cell-based regenerative medicine is that it may be possible to avoid the side effects that can be caused by other stem cell stimulators, such as growth factors and cytokines. In addition, each protein component brings with it some additional biological effects that positively affect tissue regeneration. Thus, PALP has anti-cancer effects and promotes the efficacy of chemotherapy in addition to its ability to promote the proliferation and survival of stem cells and progenitor cells. PALP also decreases blood sugar level in animal models of hyperglycemia.

TF is known to promote the viability of normal cells including stem cells and progenitor cells as well as the formation of blood vessels; both processes are important for maintaining viability of the newly regenerated tissue.

AT promotes proliferation of myoblasts and pre-adipocytes as well as exerts anticancer effects. PALP, TF and AT generally enhance each other's effects on the expansion of progenitor and stem cells in vitro. Accordingly, as demonstrated in the application, PALP+TF and PALP+TF+AT promoted bone marrow regeneration both from endogenous and transplanted bone marrow cells following partial and complete destruction of bone marrow, respectively.

One embodiment of the invention includes a growth or isolation media for the isolation and cultivation of stem cells or progenitor cells including PALP without or with TF and, optionally, AT.

Another embodiment of the invention provides a method for simultaneous administration to the mammal stem/progenitor cells PALP in the absence or presence of TF and, optionally, AT to enhance viability of transplanted cells. In other embodiments, the amounts of proteins are sufficient to simultaneously enhance both the viability of transplanted cells and proliferation of tissue resident stem/progenitor cells in the damaged tissue. In another embodiment the transplanted stem cells are hematopoietic stem/progenitor or mesenchymal stem/progenitor cells that are either purified or present in a non-fractionated or partially purified bone marrow preparation. In yet another embodiment the transplanted cells are embryonic stem cells or stem/progenitors cells isolated from specific tissues other than bone marrow.

Another embodiment of the invention provides a method to stimulate proliferation and survival of tissue resident stem cells and stem cell-derived progenitor cells (including myoblasts or pre-adipocytes) by administering to the mammal PALP in the absence or presence of TF and, optionally, AT.

A further embodiment of the invention includes a method to repopulate the diseased tissue, including bone marrow, with normally functioning cells from endogenous stem/progenitor cells by periodically administering to the mammal PALP with or without TF and/or AT.

An additional embodiment of the invention provides the manufacture of medicaments including PALP alone or together with TF and, optionally, AT to treat diseased tissue or improve the efficacy and safety of bone marrow transplantation.

In one embodiment, isolated stem cells or progenitor cells are expanded in a medium containing effective amounts of PALP with or without TF and, optionally, AT. The term "effective amount" means a concentration of each individual protein that in vitro enhances the number of viable cells compared to cell numbers obtained in a medium without that protein.

In another embodiment, effective amounts PALP with or without TF and, optionally, AT are used in vivo to enhance the survival and proliferation of transplanted stem/progenitor cells. "Effective amount" means a concentration of each individual protein that enhances the number of transplanted stem/progenitor cells that remain viable in vivo after the transplantation process compared to cell numbers obtained without using that protein. In a variation of this embodiment, "effective amount" also means a protein concentration that enhances both the viability of transplanted cells and the proliferation rate of stem/progenitor cells in the affected tissue.

In yet another embodiment, the mammal is administered therapeutically effective amounts of PALP with or without TF and, optionally, AT. The term "therapeutically effective amount" is used in this application to mean a dose that increases the number of tissue-resident healthy cells in the targeted diseased tissue compared to cell numbers obtained without the use of that protein.

As used herein, the term "PALP" and the phrase "human PALP" are used interchangeably to refer to placental alkaline phosphatase and the other human alkaline phosphatases. The term "active PALP" is used in this application to refer to the human alkaline phosphatase proteins and their glycosylated and non-glycosylated forms as well as peptides derived from these proteins which similarly enhance proliferation and survival of stem/progenitor cells. The terms "substantially purified" and "highly purified" are used herein to encompass preparations of PALP or another alkaline phosphatase that are obtained from a raw tissue extract (placenta or blood) by one or more purification steps, such as, for example, solvent extraction, column chromatography separation, or other separation methods. These methods may enrich the concentration of PALP, relative to the raw extract, to an extent that PALP is highly concentrated, and the remaining components do not pose any significant health risk and do not reduce the beneficial effects of PALP. The terms "substantially purified" and "highly purified" should not be construed to connote absolute purity.

The term "TF" refers to human transferrin that may or may not bind iron. The term "active TF" is used in this application to refer to the transferrin protein, its glycosylated and non-glycosylated forms, and peptides derived from these proteins which similarly enhance proliferation and survival of stem/progenitor cells. The terms "substantially purified" and "highly purified" are used herein to encompass preparations of TF that are obtained from a raw tissue extract (placenta or blood) by one or more purification steps, such as, for example, solvent extraction, column chromatography separation, or other separation methods. The terms "substantially purified" and "highly purified" should not be construed to connote absolute purity of TF.

The term "AT" refers to human $\alpha_1$-antitrypsin. The term "active AT" is used in this application to refer to the $\alpha_1$-antitrypsin protein, its glycosylated and non-glycosylated forms, and peptides derived from these proteins which similarly enhance proliferation and survival of stem/progenitor cells. The terms "substantially purified" and "highly purified" are used herein to encompass preparations of AT that are obtained from a raw tissue extract (placenta or blood) by one or more purification steps, such as, for example, solvent extraction, column chromatography separation, or other separation methods. The terms "substantially purified" and "highly purified" should not be construed to connote absolute purity of AT. The term "mammal" includes a human. The term "transplanted stem cell" may be stem cells transplanted from one to oneself, a transplant of stem cells from a genetically non-identical member of the same species, or a transplant of stem cells from one to a genetically identical other (such as an identical twin).

In one embodiment of the invention, PALP or another human alkaline phosphatase may be used alone or in the presence of TF and, optionally, AT to enhance survival and proliferation of endogenous human stem cells as well as progenitor cells, such as myoblasts and pre-adipocytes, in the target diseased tissues. Various combinations of these proteins may also be used to enhance survival and proliferation of stem cells and progenitor cells before, during, and after transplantation. A particularly valuable effect of the PALP+TF and PALP+TF+AT combinations is promotion of bone marrow regeneration from endogenous and transplanted hematopoietic stem/progenitor cells in partially and fully myeloablated hosts, respectably. Other valuable effects of these protein compositions include promotion of survival and proliferation of bone marrow-derived mesenchymal stem/progenitor cells that predictably can be used to facilitate tissue regeneration from endogenous or transplanted stem/progenitor cells.

Active Components

PALP is one of the presently known four members of the alkaline phosphatase enzyme family that hydrolyzes phosphate-containing compounds at alkaline pH [J. L. Millan, and W. H. Fishman (1995), "Biology of human alkaline phosphatases with special reference to cancer." *Critical Reviews in Clinical Sciences,* 32, 1-39]. Other members of this phosphatase group that also hydrolyze phosphate-containing compounds at alkaline pH include the tissue non-specific (liver/bone/kidney), the intestinal, and PALP-like (germ-cell) alkaline phosphatases. Mature PALP is a dimer of two identical glycosylated subunits. Each subunit has an approximate molecular weight of 66 kDa, as determined by gel electrophoresis. For simplicity, in the application the terms "PALP" and "alkaline phosphatase" are used interchangeably for all four human alkaline phosphatases.

PALP enhances both the proliferation and survival of several lines of mouse embryo fibroblasts, fibroblast-like cells derived from the lung of human fetus, and adult human fibroblasts [Q.-B. She, J. J. Mukherjee, J.-S. Huang, K. S. Crilly, and Z. Kiss (2000), "Growth factor-like effects of placental alkaline phosphatase in human fetus and mouse embryo fibroblasts," *FEBS Letters,* 468, 163-167; Q.-B. She, J. J. Mukherjee, T. Chung, and Z. Kiss (2000), "Placental alkaline phosphatase, insulin, and adenine nucleotides or adenosine synergistically promote long-term survival of serum-starved mouse embryo and human fetus fibroblasts," *Cellular Signaling,* 12, 659-665]. In an embodiment of the invention, it will be shown that PALP, particularly in the presence of TF or TF+AT also enhances proliferation and survival of human bone marrow-derived mesenchymal stem/progenitor cells as well as proliferating precursors of myotubes and adipocytes. In another embodiment of the invention, it also will be shown that PALP in combination with TF or TF+AT promotes regeneration of bone marrow from both endogenous stem/progenitor cells and transplanted bone marrow cells in partially and fully myeloablated hosts, respectively.

The tissue non-specific and intestinal alkaline phosphatases also stimulate proliferation of mouse embryo fibroblasts in the presence of 2 mM or higher concentration of calcium. One embodiment of the invention uses each human alkaline phosphatase to enhance proliferation and survival of normal stem cells and progenitor cells.

An active derivative that is a smaller fragment of a PALP amino acid sequence and demonstrates efficacy similar to that of native PALP may be synthesized or developed. It has been demonstrated that alkaline phosphatase activity is not required in native PALP to stimulate mitogenesis. For example, both digestion of PALP with the protease bromelain and elimination of alkaline phosphatase activity through mutation provided an active derivative with respect to cell proliferation [U.S. patent application Ser. No. 10/653,622, filed Sep. 2, 2003 and entitled "Use of Placental Alkaline Phosphatase to Promote Skin Cell Proliferation"; Pub. No. US 2005/0048046 A1, Pub. date, Mar. 3, 2005]. An active derivative may be formed by exchanging amino acids at critical sites, by modifying a PALP amino acid sequence or a sequence of smaller PALP peptides. Likewise, chemical or enzymatic changes in the level and position of glycosylation may maintain or enhance the effects of PALP or its derivatives. In the practice of embodiments of the present invention, modified PALP, smaller PALP-derived peptides, or modified PALP-derived peptides may be similarly effective or even more effective than native PALP. Each of these is considered to be an active derivative. In some embodiments of the present invention native glycosylated PALP and its active derivatives as well as non-glycosylated PALP and its active derivatives may be used. For simplicity, all the above potentially active derivatives of PALP are included in the term "PALP".

Human PALP, and particularly a smaller molecular weight active PALP derivative, may also be obtained by chemical synthesis using conventional methods. For example, solid-phase synthesis techniques may be used to obtain PALP or an active derivative.

Recombinant methods of obtaining suitable preparations of PALP or active PALP derivatives are also appropriate. Using the cDNA of PALP, recombinant protein may be produced by one of the many known methods for recombinant protein expression. PALP has been cloned and expressed in cells as described by Kozlenkov, et al. [Kozlenkov, A., Manes, T., Hoylaerts, M. F. and Millan, J. L. (2002), "Function assignment to conserved residues in mammalian alkaline phosphatases," *J. Biol. Chem.*, 277, 22992-22999]. Production of recombinant PALP by bacteria [Beck, R. and Burtscher, H. (1994), "Expression of human placental alkaline phosphatase in *Escherichia coli*," Protein Expression and Purification, 5, 192-197] and yeast [Heimo, H., Palmu, K. and Suominen, I. (1998), "Human placenta alkaline phosphatase: Expression in *Pichia pastoris*, purification and characterization of the enzyme," *Protein Expression and Purification*, 12, 85-92] is also a suitable method of obtaining PALP for use with embodiments of the present invention. For simplicity, recombinant PALP is also included in the term "PALP".

A preparation of human PALP may also be obtained by extraction from placental tissue. Human placenta synthesizes the enzyme during pregnancy so that toward the end of the third term, the level of PALP in the placenta tissue and the maternal and fetal blood becomes very high. Therefore, a preparation of PALP may be obtained by butanol extraction of homogenized placenta. Other methods of extraction from placental tissue are also suitable.

As with the commercially available human PALP, it may be suitable to purify the raw placental extracts of PALP before using it in certain embodiments of the present invention. Raw placental extracts may contain other proteins, lipids, proteolipids, carbohydrates, metals, vitamins, and the like that may cause unexpected side effects when administered to a patient. Therefore, it may be suitable to use a known purification method to remove these contaminants from the raw placental extract.

Raw extracts of PALP may also be treated to purify or concentrate the amount of PALP in the preparation. In some raw extracts of PALP, the relative concentration of PALP may be too low to result in an increase in the production and secretion of insulin by islets. Purified and concentrated PALP may be suitable for treatment in vivo to ensure the quality of the preparation and to exclude the health risks caused by unidentified contaminants. Thus purified preparations of PALP may have a much higher concentration of the active component than found in a raw tissue extract. Substantially purified preparations of bone-specific, tissue non-specific, and PALP-like (germ) alkaline phosphatase enzymes are all available commercially (for example, from Sigma-Aldrich).

The stimulatory effects of PALP on fibroblast proliferation in vitro may be enhanced by pre-heating it at 65-75° C. for 30 min [Q.-B. She, J. J. Mukherjee, J.-S. Huang, K. S. Crilly, and Z. Kiss (2000), "Growth factor-like effects of placental alkaline phosphatase in human fetus and mouse embryo fibroblasts," *FEBS Letters*, 468, 163-167]. Thus, a step of heat-activation may be included during the final preparation of PALP for injection.

TF, the second potential component of the stem cell-stimulating composition, is also a glycoprotein with an approximate molecular weight of 80 kDa. The structure and biological effects of TF as well as the properties of transferrin receptor have recently been reviewed [Qian, Z. M., Li, H., Sun, H. and Ho, K. (2002), "Targeted drug delivery via the transferrin receptor-mediated endocytosis pathway," *Pharmacol Rev.*, 54, 561-587]. Its major function is to carry iron from the sites of intake into the systemic circulation to the cells and tissues. However, TF also serves as a growth factor for many cell types; for this reason, it is a standard component of several growth media used for cell culture. Whether the growth factor effects of TF are always mediated by iron or not is presently unclear. TF also promotes migration of endothelial cells [Carlevaro, M. F., Albini, A., Ribatti, D., Gentili, C., Benelli, R., Cermelli, S., Cancedda, R. and Cancedda, F. D. (1997), "Transferrin promotes endothelial cell migration and invasion: Implication in cartilage neovascularization." *J. Cell. Biol.*, 136, 1375-1384].

As used herein, the term "TF" and the phrase "human TF" are used interchangeably to refer to transferrin. As used herein, active TF means the human protein, or closely related mammalian proteins, and its/their glycosylated and non-glycosylated forms as well as peptides derived from these proteins that, when administered together with PALP and/or AT, is effective to enhance the proliferation and survival of stem and progenitor cells. For these studies, partially iron-saturated (iron content: 300-600 µg per 1-g protein) that was more than 98% pure was purchased from Sigma-Aldrich (catalog numbers T 3309 according to the 2005/2006 Sigma Catalog). Because TF is a major component of human blood, and placenta always contains significant volume of blood, the placenta tissue is also a potential source for the isolation of this protein. Chromatographic separation methods are available for the purification of TF. For example, it is possible to enrich TF, along with some other glycoproteins, using a so-called Concanavalin-A-Sepharose column, which separates glycoproteins based on their ability to interact with lectins such as Concanavalin-A. This step is then followed by other column chromatography methods, such as size-exclusion chromatography, to separate glycoproteins from each other. These techniques are well within the reach of expertise of experts in the art.

The sequence of human TF (which has approximately 10 variants) is known and the corresponding cDNA is available. This allows expression of original TF or its point and deletion mutants in any cell line of choice, for example in insect cells [Tomiya, N., Howe, D., Aumiller, J. J., Pathak, M., Park, J., Palter, K. B., Jarvis, D. L., Betenbaugh, M. J. and Lee, Y. C. (2003), "Complex -type biantennary N-glycans of recombinant human transferring from Trichoplusia ni cells expressing mammalian β-1,4-galactotransferase and β-1,4-N-acetylglucosaminenyltransferase II," *Glycobiology*, 13, 23-34]. These and similar techniques may be used to generate, at larger scale, various active recombinant forms of TF and its derivatives.

The stimulatory effects of TF on fibroblast proliferation in vitro were not decreased by pre-heating it at 65-75° C. for 30 min (Zoltan Kiss, unpublished observation). Thus, pre-heating of TF-containing compositions to enhance the effects of other components, such as AT and PALP, will not alter the stimulatory effects of TF.

Most TF preparations that are commercially available contain only minor impurities comprising only 2-3% of the total protein. These commercial TF preparations can be further purified by available methods to obtain homogeneous TF by successive chromatographic steps. TF preparations containing relatively minor impurities may also be used for formulating the compositions used in the practice of the present invention, so long as the given composition comprises therapeutically effective amount of TF, and impurities are not toxic and do not interfere with the beneficial effects of the components.

Since TF is a major blood protein, and placenta tissue contains a significant volume of blood, human TF may also be obtained by extraction from placental tissue. By way of example, a TF preparation may be obtained by butanol extraction of homogenized placenta. Other methods of extraction from placental tissue are also suitable.

Raw extracts or fractions derived from the blood or placenta that are not further enriched in TF by using physical concentration methods cannot be expected to have physiological effects similar to those observed for the preparation of sufficiently enriched or purified or homogenous TF. The main reason is that in the extracts or crude fractions the relative concentration of TF will be too low to expect a readily detectable effect in the skin.

Therefore, if blood- or placenta-derived TF preparation is to be used in the practice of the embodiments of the present invention, a raw extract or fraction should be treated to enrich the concentration of TF and obtain a purified preparation. A purified preparation will have a higher concentration of the active component than found in a raw tissue or blood extract. The term "purified" is used herein to encompass compositions that are obtained from a starting material by one or more purification steps (such as solvent extraction, column separation, chromatographic separation, etc.) that enrich the concentration of TF, relative to the starting material. The term "purified TF" should not be construed to connote absolute purity of the protein.

A further consideration in the practice of some embodiments of the invention is the degree of purity that is required for the use in vitro and in vivo. An advantage of using a preparation comprising highly purified or homogeneous TF in the methods and treatment regiments of some embodiments of the present invention is that possible side effects caused by contaminating proteins will not likely be an issue during in vivo application. However, impure TF or TF that is purified but not homogeneous also can be used in the compositions described herein, particularly for in vitro applications, as long as no adverse effects are observed. Considering that every consecutive purification step, either using blood or placenta as starting material, results in some loss of the protein, using a less pure than homogeneous TF material for the compositions may be more cost-effective.

As indicated above, various molecular derivatives of TF including iron-free and iron-containing forms may be similarly active in enhancing the effects of PALP on stem/progenitor cell survival and proliferation. For simplicity, all the above mentioned potentially active derivatives of TF are included in the term "TF".

The third potential active component in the methods and compositions of some embodiments of the present invention is human $\alpha_1$-antitrypsin (AT), or an active derivative thereof As used herein, the term "AT" and the phrase human AT are used interchangeably to refer to $\alpha_1$-antitrypsin. As used herein, active AT means the various isoforms of the human protein, or closely related mammalian proteins, and its/their glycosylated and non-glycosylated forms as well as peptides derived from these proteins that, when administered together with PALP and/or TF, is effective to enhance the proliferation of stem cells and progenitor cells. For simplicity, all the potentially active derivatives of AT are included in the term "AT".

AT belongs to the large family of serine protease inhibitors, or serpins, that act as irreversible suicide inhibitors of proteases [Janciauskiene, S. (2001), "Conformational properties of serine proteinase inhibitors (serpins) confer multiple pathophysiological roles," Biochim. Biophys. Acta, 1535, 221-235]. While AT is a particularly effective inhibitor of elastase, it also inhibits other proteases such as trypsin. AT deficiency, often caused by its oxidative damage in smokers, is causally related to emphysema due to the uncontrolled action of proteases in the lung. Other physiological effects of AT may include inhibition of cancer cell proliferation [Finlay, T. H., Tamir, S., Kadner, S. S., Cruz, M. R., Yavelow, J. and Levitz, M. (1993), "$\alpha_1$-antitrypsin- and anchorage-independent growth of MCF-7 breast cancer cells," Endocrinology, 133, 996-1002].

In addition to function as a protease inhibitor, AT has also been shown to stimulate proliferation of various cell types [Perraud, F., Besnard, F., Labourdette, G. and Sensenbrenner, M. (1988), "Proliferation of rat astrocytes, but not of oligodendrocytes, is stimulated in vitro by protease inhibitors," Int. J. Devl. Neuroscience, 6, 261-266; She, Q.-B., Mukherjee, J. J., Crilly, K. S. and Kiss, Z. (2000), "$\alpha_1$-Antitrypsin can increase insulin-induced mitogenesis in various fibroblast and epithelial cell lines," FEBS Lett., 473, 33-36; Dabbagh, K., Laurent, G. J., Shock, A., Leoni, P., Papakrivopoulou, J. and Chambers, R. C. (2001), "Alpha-1-antitrypsin stimulates fibroblast proliferation and procollagen production and activates classical MAP kinase signaling pathways," J. Cell. Physiol., 186, 73-81]. As it will be demonstrated in the Examples for the first time, AT adds to the effects of PALP and TF in enhancing the proliferation of myoblasts and pre-adipocytes that are immediate precursors of differentiated muscle and fat cells, respectively. Thus, AT may be used together with PALP and TF to increase the number of differentiated cells in the diseased target tissue and perhaps to even contribute to the expansion of progenitor cells in vitro.

Relatively pure human AT, isolated from human plasma, can be purchased, for example, from Sigma-Aldrich (catalog number: A 9024). Commercial AT then can be further purified by conventional methods including various chromatographic methods. AT can also be highly purified from commercial PALP preparation that contains it as a significant contaminant. For the purpose of this application essentially pure AT, purified from commercial PALP preparation (Sigma-Aldrich) by a previously described method [She, Q.-B., Mukherjee, J. J., Crilly, K. S. and Kiss, Z. (2000), "$\alpha_1$-Antitrypsin can increase insulin-induced mitogenesis in various fibroblast and epithelial cell lines," FEBS Lett., 473, 33-36] as also described under "Examples", was used. By implication, AT can be isolated in essentially pure form from human placenta. Placenta not only produces this protein [Bergman, D., Kadner, S. S., Cruz, M. R., Esterman, A. L., Tahery, M. M., Young, B. K. and Finlay, T. H. (1993), "Synthesis of $\square_1$-antichymotrypsin and $\alpha_1$-antitrypsin by human trophoblast," Pediatric Res., 34, 312-317], but placenta-associated blood also is a rich source of AT.

The sequence of AT is known and the corresponding cDNA is available [Leicht, M., Long, G. L., Chandra, T., Kurachi, K., Kid, V. J., Mace, M. Jr., Davie, E. W. and Woo, S. L. C. (1982), "Sequence homology and structural comparison between the chromosomal human $\alpha_1$-antitrypsin and chicken ovalbumin genes," Nature, 297, 655-659; Long, G. L., Chandra, T., Woo, S. L. C., Davie, E. W. and Kurachi, K. (1984), "Complete Sequence of the cDNA from human $\alpha_1$-antitrypsin and the gene for the S variant," Biochemistry, 23, 4828-4837]. Molecular biology techniques are available to produce recombinant forms of AT, mutated forms of AT [Kwon, K.-S., Kim, J., Shin, H. S. and Yu, M.-H. (1994), "Single amino acid substitutions of $\alpha_1$-antitrypsin that confer enhancement in thermal stability," J. Biol. Chem., 269, 9627-9631], or the carboxyl-terminal fragment of AT, or any other fragment of AT [Kataoka, H., Uchino, H., Iwamura, T., Seiki, M., Nabeshima, K. and Koono, M. (1999), "Enhanced tumor growth and invasiveness in vivo by a carboxyl-terminal fragment of $\alpha_1$-proteinase inhibitor generated by matrix metalloproteinases: A possible modulatory role in natural killer cytotoxicity," *American J. Pathol.,* 154, 457-468]. These and similar techniques may be used to generate various active recombinant forms of AT and its derivatives.

The probability of significant toxic effects of AT is very low, because AT is a major protein in the human blood. Furthermore, AT is an acute phase reactant, and its level during inflammation can increase 2-3 fold without causing any recognized side effect.

The stimulatory effects of AT on fibroblast proliferation in vitro is enhanced by pre-heating it at 65-75° C. for 30 min or at 41° C. for 21 hours [She, Q.-B., Mukherjee, J. J., Crilly, K. S. and Kiss, Z. (2000), "$\alpha_1$-Antitrypsin can increase insulin-induced mitogenesis in various fibroblast and epithelial cell lines," *FEBS Lett.* 473, 33-36]. It is reasonable to assume that pre-heating may also enhance the effects of AT on the proliferation of progenitor cells and stem cells. Thus, a step of heat-activation of AT may be included during the preparation of active compositions.

AT preparations that are commercially available contain impurities. Impure commercial AT preparations can be used as starting material to obtain homogeneous AT by successive chromatographic steps, as described in detail in Example 2. Impure AT preparations may also be used in formulating the compositions for use in the practice of the present invention, so long as the given composition comprises therapeutically effective amount of AT, and impurities are not toxic and do not interfere with the beneficial effects of the components.

A preparation containing human AT may also be obtained by extraction from placental tissue. By way of example, a preparation may be obtained by butanol extraction of homogenized placenta. Other methods of extraction from placental tissue are also suitable.

Raw extracts or fractions derived from the blood or placenta that are not further enriched in AT by using physical concentration methods cannot be expected to have physiological effects similar to those observed for the preparation of sufficiently enriched or purified or homogenous AT. The main reason is that in the extracts or crude fractions the relative concentration of AT will be too low to expect a readily detectable effect on cell survival/proliferation. Another advantage of using a preparation comprising highly purified or homogeneous AT in the methods and treatment regiments of some embodiments of the present invention is that possible side effects caused by contaminating proteins will not likely be an issue. Therefore, if blood- or placenta-derived AT preparation is to be used in the practice of some embodiments of the present invention, a raw extract or fraction should be treated to enrich the concentration of AT and obtain a purified preparation. A purified preparation will have a higher concentration of the active AT component than found in a raw tissue or blood extract. The term "purified" is used herein to encompass compositions that are obtained from a starting material by one or more purification steps (such as solvent extraction, column separation, chromatographic separation, etc.) that enhance the concentration of AT, relative to the starting material. The term "purified AT" should not be construed to connote absolute purity of the protein.

Use of commercial PALP preparation without further processing to stimulate proliferation and survival of stem cells and progenitor cells in vitro and in vivo.

Figure 2:
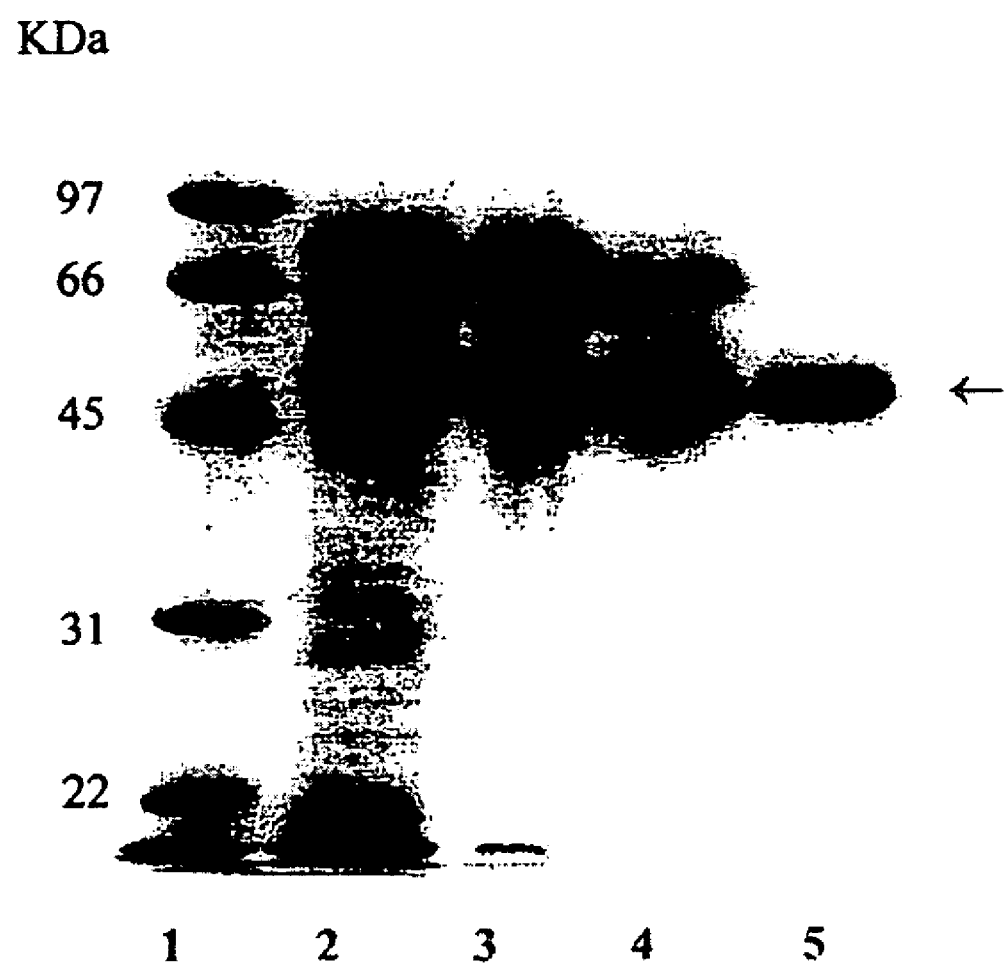
FIG. 2 shows a digital image of a gel separation, demonstrating that the $\alpha_1$-antitrypsin used for the experiments, except when indicated otherwise, was homogeneous, i.e. did not contain any other stained component. The image also shows that the protein composition of the starting commercial PALP preparation is slightly different compared to the starting material used for FIG. 1. Here, in addition to the three major bands, represented by TF (80 kDa), a mixture of albumin and PALP (66-68 kDa), and AT (52 kDa), there were several minor lower molecular weight proteins as well.

As shown in FIG. 1 and FIG. 2, the commercial PALP preparation from Sigma Aldrich contains 3 major bands (~80 kDa, ~66-68 kDa, and ~52 kDa, respectively) and occasionally several lower molecular weight minor bands as well (FIG. 2). As determined by sequence analysis at the Mayo Clinic's Core Facility (Rochester, Minn.) and a similar facility in the Department of Medicinal Chemistry at Szeged University (Szeged University, Hungary), the 80 kDa band is represented by TF, the 66-68 kDa band is composed of albumin and PALP in a ratio of about 3:1, and the 52 kDa band is represented by AT. One minor band (~43-45 kDa) is represented by $\alpha_1$-acid glycoprotein, while the rest are proteolytic degradation products of TF.

Since this commercial preparation contains only human proteins and their degradation products that are not known to trigger any side effects, this PALP product may be used as it is both in vivo and in vitro to enhance proliferation and survival of stem/progenitor cells.

Use of dialysis and/or spin cartridge technology to produce protein compositions from the commercial PALP preparation.

The commercial PALP in solution may also be dialysed using a tube made of dialysis membrane with a 50 kDa cut off (i.e. the membrane pores allow efflux of those proteins that have molecular mass below 50 kDa). Such dialysis tube would retain only those proteins that have a molecular mass higher than 50 kDa. Thus, after dialysis the remaining solution will only contain TF, albumin, PALP and AT.

Using a spin cartridge from Agilent Technologies, TF, albumin, or AT or any other protein from a solution may be removed. The cartridges use one type of affinity-purified polyclonal antibody or a mixture of various antibodies that bind the respective protein(s). Using a simple low-speed centrifugation step, the antibody-bound protein(s) can be removed so that only the protein of interest remains in the solution. This method allows the production of albumin-free protein solutions in any combination including PALP, TF, and AT alone as well as mixtures of PALP+TF, PALP+ATP, TF+AT and PALP+TF+AT faster and more cost effectively than using more traditional separation methods. Such antibody-based cartridges may be used after removing lower molecular weight contaminants by dialysis.

Compositions and Methods of Treatments

Compositions to Stimulate Proliferation of Endogenous Stem Cells and Progenitor Cells in the Target Diseased Tissue.

To achieve increased proliferation of endogenous stem cells and progenitor cells in the diseased tissue, PALP with or without TF and, optionally, AT may be applied via intravenous, intraarterial, intraportal, intradermal, intraperitoneal, subcutaneous, intra-tissue or intramuscular delivery routes. In some embodiments, these proteins may be delivered using a minipump inserted under the skin. In other embodiments, these proteins may be expressed endogenously in the lung or liver via delivering the corresponding DNA sequences by a suitable, for example retroviral, vector.

The diseased tissue may be, for example, the heart, liver, kidney, muscle, fat, lung, skin, pancreas, the central nervous system, gastrointestinal tract, blood, spleen, cartilage, and bone marrow. The stem/progenitor cells may be tissue resident or may derive from the bone marrow.

The injectable solution may be prepared by dissolving or dispersing a suitable preparation of the active protein component(s) in the carrier using conventional methods. A suitable dosage for systemic administration may be calculated in grams of the active agent(s) per square meter of body surface area for the subject. In one embodiment, the therapeutically effective amount of each protein is between about 0.01 to 2.0 g of the individual protein per $m^2$ body surface of the mammal. In another embodiment, the therapeutically effective amount of PALP is between 0.1 to 1 g per $m^2$ body surface of the mammal. The amount of each protein may vary between 0.01-2.0-g per m² of body surface depending on whether the method of application is systemic (intravenous, intraarterial, intraperitoneal) or more local (for example, subcutaneous, intraportal, intradermal, intra-tissue, or intramuscular). The amount also depends on the nature of the protein. Since in cell experiments considerably more AT than PALP is needed to stimulate cell proliferation, the injected solution will also contain more AT than PALP or TF.

The proteins are dissolved in a physiologically compatible solution. For example, 0.9% NaCl (physiological saline) or phosphate buffered saline is appropriate to prepare the proteins for injection. As examples only, a suitable composition for the practice in the method comprises an alkaline phosphatase in a 0.9% physiological saline solution to yield a total protein concentration of 5 mg/ml. Another suitable solution includes PALP in a 0.9% physiological saline solution to yield a total protein concentration of 20 mg/ml. A third solution includes PALP in a 0.9% physiological salt solution to yield a total protein concentration of 50 mg/ml. Other compositions may contain TF and, optionally, AT each at 5-50 mg/ml concentrations. The concentrations of PALP, TF and AT, if applied together, may be different as discussed above. In some embodiments, PALP may be enclosed in liposomes such as immunoliposomes, or other delivery systems or formulations.

Application of PALP with or without TF and AT by one of the above application methods may be repeated as many times as needed to achieve a satisfactory level of re-population of the target diseased tissue by normally functioning differentiated cells.

In one embodiment, the therapeutically effective amount of PALP with or without TF and AT may be administered once daily. In another embodiment, the dose is administered twice or three times weekly. In still another embodiment, administration is performed once a week or biweekly. Since the half-life time of each protein is relatively long (4-6 days), one suitable application is twice a week or once a week. The similarly long half-life time of these proteins also allows their simultaneous application that is more practical than their separate applications.

The injectable solution may be modified by one or more additive(s) or enhancer(s) that positively influence(s) the proliferation and survival of normal tissues. Examples of such additives and enhancers include growth factors including insulin like growth factor-1, insulin, growth hormone, platelet-derived growth factor, fibroblasts growth factor, placental growth factor, epidermal growth factor, vascular endothelial growth factor, transforming growth factors as well as testosterone and amino acids such as leucine. Generally these agents enhance cell proliferation and survival as well as protein synthesis in the muscle, adipose tissue and other tissues. In addition, PALP with and without TF and AT may also be administered together with nutraceuticals, such as freeze-dried blueberry extract, green tea extract, camosine, catechin and the activated form of vitamin $D_3$. These nutraceuticals were shown to enhance proliferation of human bone marrow-derived hematopoietic stem cells [Biskford, P. C., Tan, J., Shytle, R. D., Sanberg, C. D., El-Badri, N. and Sanberg, P. R. (2006), "Nutraceuticals synergistically promote proliferation of human stem cells," Stem Cells and Development, 15, 118-123].

Compositions and Methods for the Expansion of Stem/Progenitor Cells in vitro.

Isolated stem cells and progenitor cells can be maintained and propagated in a cell culture growth medium. Among many possibilities, a suitable medium is Dulbecco's modified Eagle's medium supplemented with 1-10% (v/v) fetal calf serum and antibiotics. Highly purified PALP from 1 μg per ml up to about 50 μg per ml may be added alone to the medium to reduce cell death and accelerate cell proliferation. Alternatively, to enhance viability and cell proliferation PALP may be added to the medium together with 1-50 μg per ml of highly purified human TF (iron containing or iron-free) and/or 10-500 μg per ml of highly purified human AT. Since each protein is water soluble, they can be dissolved in any water-based solution that is compatible with the cell culture conditions. Preferably, stock solutions (0.01-1 mg/ml) of the proteins are dissolved in the same medium in which the cells are cultured.

The effective amounts of PALP, TF and AT may depend on the rate of purification of the given protein. By example, if less purified commercial PALP is used in the practice, its concentration in the isolation and culture media will be in the range of 10-200 μg/ml. Similarly, less purified AT preparations may require up to 1,000 μg/ml concentration for an optimum effect.

Compositions and Methods to Promote Survival of Stem/Progenitor Cells before, during, and after Transplantation.

PALP without or with TF and, optionally, AT may be used for any stem/progenitor cell transplantation event to enhance the survival and expansion of transplanted cells with the eventual goal of repopulating the diseased tissue with normally functioning differentiated cells. After harvesting the stem/progenitor cells for transplantation, PALP/TF/AT can affect all three major steps of the transplantation process, i.e. cell expansion if needed and preparation of cells for transplantation, infusion of transplant, and expansion of transplanted cells following engraftment (homing to the target tissue).

In some cases, in vitro expansion of stem/progenitor cells in a serum-containing medium prior to transplantation is needed. As discussed above, PALP without or with TF and AT may also be present during that incubation phase. To make sure that no infectious agents are co-transplanted, several days or weeks prior to transplantation the serum-containing medium is changed for a serum-free medium containing PALP without or with TF and, optionally, AT. The serum-free medium may also contain any human growth factor or growth factor-like substance that promotes survival and/or proliferation of stem/progenitor cells and do not interfere with the similar promoting effects of PALP, TF and AT. Propagation in a serum-free medium, including one or more medium changes, is required for as long as needed to reduce contamination of cells by any foreign agent to an acceptable, preferably a non-detectable, level. The role of PALP as well as TF and AT during that time period is to safely retain or even further increase the number of transplantable cells. Concerning the concentration of these proteins in the medium the same applies that was described under "Compositions and methods for the expansion of stem/progenitor cells in vitro".

Stem/progenitor cells prepared for transplantation are suspended in a serum-free medium. Stem/progenitor cells can be embryonic stem cells or adult stem/progenitor cells. Adult stem/progenitor cells may be obtained directly from the bone marrow (for example, from posterior iliac crests), any other tissue, or from peripheral blood. In the latter case, the donor may be pretreated with granulocyte colony-stimulating factor and/or granulocyte-macrophage colony stimulating factor to mobilize bone marrow cells and enhance the yield of peripheral blood progenitor cells. The stem/progenitor cell population may be enriched by various methods, for example by using magnetic-activated cell sorting to remove monocytes or T-lymphocytes or Ficoll-Hypaque density gradient centrifugation. Prior to transplantation, the stem/progenitor cells are usually stored in a 5-20% dimethylsulfoxide-containing medium such as Iscove's modified Dulbecco's medium in the vapor phase of liquid nitrogen. Standardized procedures for the isolation, enrichment and storage of stem/progenitor cells are well known in the art; review of these articles or improvement any of these procedures is not within the scope of this invention.

In some embodiments, PALP with or without TF and AT is included in the cell-containing infused solution. The proteins are dissolved in the same solution that is used for the infusion. For example, Iscove's modified Dulbecco's medium or 0.9% NaCl (physiological saline) is an appropriate solute for infusion. The amount of each protein may vary between 0.01-2.0-g per m of body surface depending on the method of application and the location of the target tissue. For example, if an endogenous organ is targeted via simultaneous intravenous application of stem/progenitor cells and the specific protein composition, then the amounts of proteins are likely to be closer to the 2.0-g per m$^2$ value. However, if the cells and proteins are used to replace damaged skin or muscle cells via intradermal or intramuscular applications, then the amounts of proteins will be closer to the lower end of the 0.01-2.0-g per m concentration range. In some embodiments, the protein compositions may also be delivered intravenously, intraperitoneally, subcutaneously, intraarterially, intraportally, intradermally or by any other method (for example, using a minipump) that ensures their accumulation in the targeted diseased tissue.

Transplantation of the stem/progenitor cells will likely to be a single event in most cases due to the limited supply of cells. However, application of the same or less amounts of PALP with or without TF and, optionally, AT by one of the above application methods may be repeated as many times as needed to ensure the survival and in vivo propagation of the transplanted cells. For example, in case of subjects receiving bone marrow-derived stem/progenitor cell transplantation, PALP without or with TF and AT may be administered for up to about 40 days on a regular basis (twice or thrice a week) for promoting regeneration of bone marrow. With respect to the addition of additives and enhancers together with PALP/TF/AT after stem/progenitor stem cell transplantation the same applies that is described for stimulating the survival and proliferation of endogenous stem/progenitor cells.

EXAMPLES

Example 1

Purification and Spectrophotometric Assay of PALP

Human PALP (Type XXIV, 1020 units of total activity) in a partially purified form was obtained commercially from Sigma-Aldrich. A butanol extraction of placental tissue, followed by one or more chromatographic steps, was performed by Sigma-Aldrich to obtain the partially purified material.

As determined by sodium dodecyl sulfate-polyacrylamide gel electrophoresis (SDS-PAGE), the partially purified PALP obtained from Sigma-Aldrich (denoted "commercial PALP" herein) was not homogeneous and contained other proteins. FIG. 1 shows a picture of a gel separation of a preparation comprising commercial PALP without further purification, and other preparations of PALP of increasing purity. Separation of proteins was performed by conventional SDS-PAGE, and proteins were stained with coomassie blue stain. Lane 1 contains various molecular mass standards for comparison. Lane 2 represents a preparation containing commercial PALP with a strong 52 kDa band representing AT and another strong 66 kDa band representing a mixture of PALP and albumin. Lanes 3 and 4 represent preparations comprising commercial PALP material after further purification steps (described below), and lane 5 represents a preparation of homogeneous PALP obtained by the complete purification procedure described below.

A purification procedure was performed to further purify the commercially obtained PALP to homogeneity. A slightly modified procedure described earlier [She, Q.-B., Mukherjee, J. J., Huang, J.-S., Crilly, K. S. and Kiss, Z. (2000), "Growth factor-like effects of placental alkaline phosphatase in human and mouse embryo fibroblasts," *FEBS Lett.*, 469, 163-167] was used which are incorporated by reference.

The solution of commercial PALP was prepared by dissolving 350 mg of commercial PALP into 10 ml of buffer A (0.1 M sodium acetate, 0.5 M NaCl, 1 mM MgCl$_2$, 1 mM CaCl$_2$, adjusted to pH 6.5). This solution was then further purified by successive Concanavalin A-Sepharose and Q-Sepharose chromatography as indicated earlier by Chang et al. Chang, T.-C., Huang, S.-M., Huang, T.-M. and Chang, G.-G. (1992), "Human placenta alkaline phosphatase: An improved purification procedure and kinetic studies," *Eur. J. Biochem.*, 209, 241-247] followed by t-butyl hydrophobic interaction chromatography as described by She et al [She, Q.-B., Mukherjee, J. J., Huang, J.-S., Crilly, K. S. and Kiss, Z. (2000), "Growth factor-like effects of placental alkaline phosphatase in human and mouse embryo fibroblasts," *FEBS Lett.*, 469, 163-167] except that this last step was repeated in about 60% of cases (to eliminate traces of contaminant protein) in some embodiments of the invention.

First, the PALP solution was passed through a Concanavalin A-Sepharose column followed by an elution step using buffer A (50 mM α-methyl-D-mannopyranoside) as solvent. The active fractions collected from the effluent were pooled and dialyzed against buffer B (50 mM Tris-HCL at pH 7.7). SDS-PAGE separation of the collected and dialyzed fraction is shown in FIG. 1 in lane 3.

The collected and dialyzed fraction from the previous step was then passed through a Q-Sepharose column. The fraction of interest was eluted with buffer B using a linear gradient of 0-250 mM potassium phosphate at a pH of 7.5. The active fractions from the Q-Sepharose column were pooled and dialyzed against phosphate-buffered saline and concentrated by Amicon ultrafiltration. SDS-PAGE separation of the collected and dialyzed fraction is shown in FIG. 1 in lane 4, which demonstrates that at least two major proteins are still present in the fraction after dialysis.

Then, the collected and dialyzed fraction from the previous step was purified to homogeneity by t-butyl hydrophobic interaction chromatography (HIC). Prior to adding the fraction to the t-butyl HIC column, the fraction was made 2 M in ammonium sulfate, and the pH was adjusted to 6.8. The 5-ml bed volume t-butyl HIC cartridge (BIO-RAD, Hercules, Calif.) was connected to a fast performance liquid chromatography (FPLC) system from PHARMACIA (Peapack, N.J.). The fraction was introduced to the HIC column, and the column was eluted with buffer C (100 mM sodium phosphate buffer, 2 M ammonium sulfate at pH 6.8). The column was eluted with buffer C until a first protein-containing fraction completely eluted, and then a negative gradient of 2 M-to-0 M ammonium sulfate in 100 mM sodium phosphate at pH 6.8 was passed over the column. The negative linear gradient was used to elute a second protein-containing fraction, which contained the active PALP protein.

The enzymatically active PALP fraction from the HIC separation was dialyzed against phosphate buffered saline and concentrated by Amicon ultrafiltration. The presence and purity of the PALP enzyme in the fraction was confirmed by SDS-PAGE. After electrophoretic separation, the gel was stained using coomassie blue or silver stain for visual observation of protein bands. When a single protein band with an approximate molecular weight of 66 kDa was not observed, the last chromatographic step was repeated. The pure PALP was further identified by sequence analysis performed by the Mayo Clinic Protein Core Facility (Rochester, Minn., US).

PALP enzyme activity was assayed using a spectroscopic method by monitoring the hydrolysis of 4-nitrophenylphosphate (as an increase in absorbance at 410 nm) at room temperature (22° C.) as described in Chang, G.-G., Shiao, M.-S., Lee, K.-R. and Wu, J.-J. (1990), "Modification of human placental alkaline phosphatase by periodate-oxidized 1,$N^6$-ethenoadenosine monophosphate," Biochem. J., 272, 683-690. Activity analysis of 5-10 μg purified enzyme was performed in 1 mL incubation volume containing 50 mM $Na_2CO_3$/$NaHCO_3$, 10 mM $MgCl_2$, 10 mM 4-nitrophenylphosphate at pH 9.8. The extinction coefficient of 4-nitrophenol was taken as $1.62 \times 10^4$ $M^{-1}$ $cm^{-1}$. An enzyme activity of 1 U (unit) is defined as 1 μmol substrate hydrolyzed/min at 22° C. at pH 9.8.

Example 2

Production of Recombinant PALP

Recombinant PALP was produced following a known procedure described in Kozlenkov, A., Manes, T., Hoylaerts, M. F. and Millan, J. L. (2002), "Function assignment to conserved residues in mammalian alkaline phosphatases," J. Biol. Chem., 277, 22992-22999, which is hereby incorporated by reference.

Example 3

Purification of AT

A partially purified human placental alkaline phosphatase preparation (PALP) was acquired from Sigma-Aldrich, Inc. AT is a major contaminant of the commercially obtained PALP. AT was first further purified by successive Concanavalin A-Sepharose and Q-Sepharose chromatography as described by Chang et al. for the isolation of PALP [Chang, T.-C., Huang, S.-M., Huang, T.-M. and Chang, G.-G. (1992), "Human placenta alkaline phosphatase: An improved purification procedure and kinetic studies," Eur. J. Biochem., 209, 241-247]. The Q-Sepharose fraction, which still contained placental alkaline phosphatase in addition to AT, was further purified to homogeneity by t-butyl HIC chromatography [She, Q.-B., Mukherjee, J. J., Crilly, K. S. and Kiss, Z. (2000), "$\alpha_1$-Antitrypsin can increase insulin-induced mitogenesis in various fibroblast and epithelial cell lines," FEBS Lett., 473, 33-36]. The 5 ml bed volume t-butyl HIC cartridge was connected to a PHARMACIA FPLC system and the fractions containing AT were pooled. The purity was confirmed by SDS-PAGE (polyacrylamide gel electrophoresis) using coomassie blue stain. The purified protein was identified as AT by sequence analysis. The sequence analysis was performed by the Mayo Clinic Protein Core Facility (Rochester, Minn., USA). The protein concentration was determined by the Lowry assay, using bovine serum albumin as standard, with a protein assay kit from Sigma-Aldrich, Inc. according to the instructions. This purification procedure has been previously published [She, Q.-B., Mukherjee, J. J., Crilly, K. S. and Kiss, Z. (2000), "$\alpha_1$-Antitrypsin can increase insulin-induced mitogenesis in various fibroblast and epithelial cell lines," FEBS Lett., 473, 33-36].

FIG. 2 is an image of a stained gel. The gel includes the commercially obtained partially purified placental alkaline phosphatase preparation (shown in lane 2) further purified by successive Concanavalin A-Sepharose (lane 3), Q-Sepharose (lane 4), and t-butyl HIC chromatography using 2 M-to-0 M ammonium sulfate gradient (lane 5). Lane 1 contains molecular mass standards of 97 kDa (top), 66 kDa, 45 kDa, 31 kDa, and 22 kDa (bottom) in that order. FIG. 2 demonstrates that while the commercial preparation contains three major proteins (one of them is AT as indicated by the arrow, while a ~66 kDa band represents PALP) and several minor proteins, the purified preparation contains only AT.

Example 4

Use of the MTT Assay to Determine Cell Viability

In some of the Examples, an MTT assay was used to determine the relative number of viable cells after treatments. The steps of this assay are described in Carmichael, J, De Graff, W. G., Gazdar, A. F., Minna, J. D. and Mitchell, J. B. (1987), "Evaluation of tetrazolium-based semiautomated colorimetric assay: Assessment of chemosensitivity testing," Cancer Res., 47, 936-942, which is hereby incorporated by reference. This colorimetric assay is based on the ability of living cells, but not dead cells, to reduce 3-(4,5-dimethyl thiazol-2-yl)-2,5-diphenyltetrazolium bromide. For this assay, cells were plated in 96-well plates, and the MTT assay was performed as described in the above article both in untreated and treated cell cultures. The MTT assay also was performed at the time when the treatment was started to allow for assessment of the proliferation and survival rates in the control and treated cell cultures. Absorption was measured at wavelength 540, indicated in the Tables below as $A_{540}$. In the MTT assay, higher values mean proportionally higher numbers of viable cells.

Example 5

Cell Lines and Cell Culture Reagents

Fetal bovine serum (FBS), fetal calf serum (FCS), and all tissue culture media were obtained from Life Technologies (formerly GIBCO BRL) (Rockville, Md.). L6 skeletal muscle myoblasts (ATCC CRL1458) were cultured in Dulbecco's modified Eagle's medium (DMEM) supplemented with 10% FBS. The 3T3-L1 mouse embryo preadipocyte cell line (ATCC CCL-92.1) was maintained in DMEM containing 10% FCS. L6 myoblasts and the differentiated myofibrils derived from them are widely used model systems to study the mechanisms involved in either maintaining the proliferative state or promote their commitment to myogenic differentiation [Kimball, S. R., Shantz, L. M., Horetsky, R. L. and Jefferson, L. S. (1999), "Leucine regulates translation of specific mRNA in L6 myoblasts through mTOR-mediated changes in availability of eIF4E and phosphorylation of ribosomal protein S6," J. Biol. Chem., 274, 11647-11652; DeArcangelis, V., Coletti, D., Conti, M., Lagarde, M., Molinaro, M., Adamo, S., Nemoz, G. and Naro, F. (2003), "IGF-I-induced differentiation of L6 myogenic cells requires the activity of cAMP-phosphodiesterase," Mol Biol. Cell, 14, 1392-1404]. On the other hand, 3T3-L1 preadipocytes and the differentiated adipocytes derived from them are frequently used model systems to study the selective mechanisms required for either maintaining the proliferative state or inducing their commitment to adipogenic differentiation [Guilherme, A., Emoto, M., Buxton, J. M., Bose, S., Sabini, R., Theurkauft, W. E., Leszyk, J. and Czech, M. P. (2000), "Perinuclear localization and insulin responsiveness of GLUT4 requires cytoskeletal integrity in 3T3-L1 adipocytes," *J. Biol. Chem.*, 275, 38151-38159].

Example 6

Isolation and Maintenance of Human Bone Marrow-derived Mesenchymal Stem Cells

Bone marrow aspirates were taken from normal adult donors after informed consent according to a protocol approved by the local Ethics Committee at the National Medical Center, Budapest, Hungary. For the preparation of bone marrow mesenchymal stem cells, essentially a widely used technique was used as described earlier by others [Pittenger, M. F., Mackay, A. M., Beck, S. C., Jaiswal, R. K., Douglas, R., Mosca, J. D., Moorman, M. A., Simonetti, D. W., Craig, S. and Marshak, D. R. (1999), "Multilineage potential of adult human mesenchymal stem cells," *Science*, 284, 143-147]. Briefly, nucleated cells were isolated with a pre-prepared commercial density gradient (Lymphoprep, Nycomed, Pharma, Oslo, Norway) and resuspended in Dulbecco's modified Eagle's medium (DMEM) (GIBCO, Grand Island, N.Y.) supplemented with 10% fetal calf serum (FCS), 50 U/ml of penicillin, and 50 μg/ml of streptomycin (GIBCO). All nucleated cells were plated in 25-cm$^2$ flasks (BD Falcon, Bedford, Mass.) at 37° C. in humidified atmosphere containing 5% $CO_2$. After 24 hours, nonadherent cells were removed and cryopreserved in liquid nitrogen until use. The remaining adherent cells were thoroughly washed with Hanks balanced salt solution (HBSS) (GIBCO). Fresh complete culture medium was added and replaced every 3 or 4 days (twice a week). When cells grew to about 80% confluence, they were suspended and harvested by incubating with a ready-made solution containing 0.25% trypsin and 1 mM EDTA (Sigma-Aldrich, St. Louis, Mo.) for 5 minutes at 37° C.; this cell suspension is designated as passage 1. These cells were further expanded with 1:3-1:5 splitting in 175-cm$^2$ flasks (BD Falcon). In the studies reported in some embodiments of the invention, mesenchymal stem cells were used between passages 3-8.

The total numbers of nucleated and viable cells were determined with a hemocytometer, using Turck's solution and trypan blue stain, respectively. The morphology of mesenchymal stem cells was examined every week under an inverted microscope (Olympos CK2, Tokyo, Japan) to verify that cells retained their structural characteristics.

Example 7

PALP Enhances Proliferation of L6 Myoblasts

L6 myoblasts were seeded in 96-well plates. After 24 hours (0 hour), when cell cultures were at ~25-30% confluence, the medium was changed to 2% serum-containing medium. Cells were then treated with highly purified PALP (pPALP), recombinant PALP (rPALP), or commercial (Sigma-Aldrich) PALP followed by incubations for 72 hours. The relative number of viable cells ($A_{540}$) was determined by the MTT assay described above. The data, shown in TABLE 1, are expressed as mean values±std. dev. of 8 determinations. The results indicate that both purified and recombinant PALP signifi- cantly enhanced proliferation of L6 cells; however, their effects were somewhat less than that observed with commercial PALP.

TABLE 1

PALP promotes proliferation of L6 myoblasts.

| Addition | Relative cell number, $A_{540}$ |
|---|---|
| Control, 0 hour | 0.777 ± 0.056 |
| Control, 72 hours | 1.185 ± 0.137 |
| pPALP, 20 μg/ml, 72 hours | 1.590 ± 0.160 |
| rPALP, 20 μg/ml, 72 hours | 1.616 ± 0.202 |
| Sigma PALP, 50 μg/ml, 72 hours | 1.992 ± 0.242 |

Example 8

Combination of PALP and Insulin Enhances Proliferation and Survival of L6 Myoblasts L6 myoblasts were seeded in 96-well plates. After 24 hours (0 hour), when cell cultures were at ~25-30% confluence, the medium was changed to 2% serum-containing medium and then treated with 50 nM human recombinant insulin, available from Calbiochem in the absence or presence of increasing concentrations of purified PALP. The relative number of viable cells (expressed as $A_{540}$) was determined by the MTT assay. The data, shown in TABLE 2, are expressed as mean values±std. dev. of 8 determinations. The results indicate that insulin and 5-15 μg/ml concentrations of PALP had stimulatory effects on cell proliferation.

TABLE 2

Both PALP and insulin enhance proliferation of L6 myoblasts.

| | Relative cell number, $A_{540}$ | |
|---|---|---|
| PALP | No Insulin | +Insulin |
| Control, 0 hour | 0.455 ± 0.026 | — |
| Control, 72 hours | 0.965 ± 0.117 | 1.646 ± 0.131 |
| PALP 2 μg/ml, 72 hours | 1.039 ± 0.148 | 1.619 ± 0.119 |
| PALP 5 μg/ml, 72 hours | 1.336 ± 0.216 | 1.613 ± 0.151 |
| PALP 15 μg/ml, 72 hours | 1.518 ± 0.175 | 1.508 ± 0.144 |
| PALP 30 μg/ml, 72 hours | 1.544 ± 0.177 | 1.625 ± 0.146 |

Example 9

PALP Enhances Survival of L6 Myoblasts

The L6 myoblasts were used at about 50% confluence, when the medium was changed to serum-free medium and incubations continued for 6 days in the absence of PALP or in the presence of purified PALP. The relative number of viable cells ($A_{540}$) was determined by the MTT assay. The data, shown in TABLE 3, are expressed as mean values±std. dev. of 8 determinations. Incubation of myoblasts in serum-free medium resulted in large decreases in cell number; such decrease in cell numbers was prevented by PALP.

TABLE 3

PALP prevents serum-free medium-induced reduction in myoblast number.

| PALP | Relative cell number, $A_{540}$ L6 myoblasts |
|---|---|
| Control, 0 hour | 0.583 ± 0.031 |
| Control, 72 hours | 0.214 ± 0.051 |
| PALP, 15 µg/ml | 0.661 ± 0.038 |

Example 10

Combined Effects of PALP, TF and AT on the Proliferation of L6 Myoblasts

In the 3 related experiments (Exp. 1, Exp. 2, Exp. 3), L6 myoblasts were seeded at $8 \times 10^5$ cells/well in 96-well plates in 10% FBS containing DMEM (low glucose) medium. After about 24 hours (~30% confluence) the medium was changed for 2% serum medium. After another 2 hours, the cells were treated with either purified PALP, or commercial partially iron-saturated TF (Sigma; T 3309), or purified AT (purified from commercial PALP preparation by the previously published procedure). PALP and TF were used at 15 µg/ml concentration, while AT was used at 150 µg/ml concentration. After 72 hours of incubation, the MTT assay was performed. The relative number of viable cells ($A_{540}$) was determined by the MTT assay. The data, shown in TABLE 4, are expressed as mean values±std. dev. of 8 determinations.

The results show that when used alone, both PALP and TF, but not AT, enhanced proliferation of L6 myoblasts. PALP and TF had somewhat less than additive effects while AT did not add to the effect of PALP. However, AT enhanced the combined effects of PALP and TF. Overall, the results indicate that the most effective stimulation of L6 myoblast proliferation occurs when all 3 proteins are simultaneously presented to the cells.

TABLE 4

PALP, TF and AT have the largest stimulatory effect on L6 myoblast proliferation when used in combination.

| | Relative cell number ($A_{540}$) | | |
|---|---|---|---|
| Treatment: | Exp. 1 | Exp. 2 | Exp. 3 |
| Control, 0 hour | 0.261 ± 0.016 | 0.277 ± 0.012 | 0.261 ± 0.015 |
| Control, 72 hours | 0.457 ± 0.034 | 0.345 ± 0.019 | 0.421 ± 0.020 |
| PALP | 0.716 ± 0.031 | 0.538 ± 0.024 | 0.625 ± 0.075 |
| TF | 0.680 ± 0.051 | 0.462 ± 0.028 | 0.609 ± 0.094 |
| AT | 0.571 ± 0.067 | 0.369 ± 0.050 | 0.508 ± 0.079 |
| PALP + AT | 0.748 ± 0.039 | 0.558 ± 0.056 | — |
| PALP + TF | — | — | 0.764 ± 0.136 |
| PALP + AT + TF | 0.833 ± 0.054 | 0.652 ± 0.053 | 0.873 ± 0.083 |

Example 11

Stimulation of Proliferation of 3T3-L1 Cells by PALP and Insulin

In this example, 3T3-L1 preadipocytes were seeded into 96-well plates at 2,000 cells per well. After 24 hours, the medium was changed to 2% serum-containing medium, followed by the addition of purified PALP at concentrations as shown below or insulin (50 nM; Calbiochem) or PALP and insulin. The incubations were then continued for 72 hours. The relative number of viable cells ($A_{540}$) was determined by the MTT assay. The data, shown in TABLE 5, are expressed as mean values±std. dev. of 8 determinations.

The results indicate that while PALP clearly stimulated the proliferation of 3T3-L1 cells, insulin alone had a relative smaller stimulatory effect. However, PALP and insulin enhanced cell proliferation of L1 cells in a synergistic manner.

These results suggest that when a pathological condition results in the death of adipocytes, administration of PALP may help to restore the number of adipocytes by increasing the number of preadipocytes. These results also suggest that PALP may be more effective at higher insulin and possibly IGF-1 levels.

TABLE 5

PALP and insulin stimulate proliferation of 3T3-L1 cells.

| | $A_{540}$ | |
|---|---|---|
| PALP | No Insulin | Insulin, 50 nM |
| Control, 0 hour | 0.591 ± 0.040 | — |
| Control, 72 hours | 0.814 ± 0.032 | 0.957 ± 0.040 |
| PALP, 2.5 µg/ml, 72 hours | 0.928 ± 0.046 | 1.113 ± 0.074 |
| PALP, 5.0 µg/ml, 72 hours | 1.234 ± 0.065 | 1.424 ± 0.119 |
| PALP, 15.0 µg/ml, 72 hours | 1.282 ± 0.137 | 1.509 ± 0.101 |

Example 12

PALP Protects 3T3-L1 Cells in Serum-Free Medium

3T3-L1 cells were seeded into 96-well plates at 8,000 cells/well. After the cells reached confluence, the medium was replaced with serum-free medium followed by treatments with purified PALP and incubations for 6 days. The relative number of viable cells ($A_{540}$) was determined by the MTT assay. The data, shown in TABLE 6, are expressed as mean values±std. dev. of 4 determinations. The results indicate that during the 6-day period, 2.5-15 µg/ml concentrations of PALP provided protection against cell death induced by serum-free medium.

TABLE 6

PALP protects 3T3-L1 cells against serum-free medium-induced cell death.

| PALP | $A_{540}$ |
|---|---|
| Control, 0 day | 1.603 ± 0.125 |
| Control, 6 days | 0.225 ± 0.022 |
| PALP, 2 µg/ml, 72 hours | 0.574 ± 0.0.45 |
| PALP, 5 µg/ml, 72 hours | 0.840 ± 0.075 |
| PALP, 10 µg/ml, 72 hours | 1.510 ± 0.131 |
| PALP, 15 µg/ml, 72 hours | 1.647 ± 0.142 |

Example 13

Commercial PALP Enhances Survival of Human Bone Marrow-Derived Mesenchymal Stem Cells in the Absence of Serum Cells were split at 1:3 and then incubated for 24 hours in 10% serum-containing medium to about 30-35% confluence. Then the medium was replaced with fresh serum-free medium. After about 2 hours, the cells remained either untreated or were treated with 1.5 µg/ml or 15.0 µg/ml of commercial PALP, as indicated in TABLE 7. Then the incubations were continued for 2, 4, 6 or 8 days followed by the determination of viable cell number. The data are expressed as mean values±std. dev. of 3 determinations. The results in TABLE 7 show that by day 6 the higher (15 μg/ml) concentration of commercial PALP nearly fully reversed, while at 8 days it fully reversed the decrease in the number of viable cells.

TABLE 7

Effects of commercial PALP on the survival of stem cells in serum-free medium.

| | Cell number per culture (×10$^{-3}$) | | |
|---|---|---|---|
| Time (days) | No PALP | PALP, 1.5 μg/ml | PALP, 15 μg/ml |
| 0 | 20 | 20 | 20 |
| 2 | 4.7 ± 3.1 | 4.8 ± 3.3 | 10.5 ± 2.6 |
| 4 | 4.6 ± 2.9 | 4.8 ± 3.1 | 12.6 ± 2.5 |
| 6 | 5.2 ± 2.7 | 5.5 ± 2.6 | 16.3 ± 3.1 |
| 8 | 6.0 ± 3.3 | 6.1 ± 3.0 | 20.1 ± 2.6 |

Example 14

Commercial PALP Enhances Proliferation of Human Bone Marrow-Derived Mesenchymal Stem Cells in the Presence of 2% Serum Cells were split at 1:3 and then incubated for 24 hours in 10% serum-containing medium to about 30-35% confluence. Then the medium was replaced with fresh medium containing 2% serum. After about 2 hours, the cells remained either untreated or were treated with 1.5 μg/ml or 15.0 μg/ml of commercial PALP, as indicated in TABLE 8. Then the incubations were continued for 2, 4 or 6 days followed by the determination of viable cell number. The data are expressed as mean values±std. dev. of 3 determinations. The results in TABLE 8 show that on each day examined, the higher (15 μg/ml) concentration of commercial PALP doubled or tripled the number of viable stem cells.

TABLE 8

Effects of commercial PALP on the proliferation of stem cells.

| | Cell number per culture (×10$^{-3}$) | | |
|---|---|---|---|
| Time (days) | No PALP | PALP, 1.5 μg/ml | PALP, 15 μg/ml |
| 0 | 20 | 20 | 20 |
| 2 | 4.1 ± 4.1 | 4.3 ± 3.8 | 8.1 ± 4.4 |
| 4 | 5.2 ± 3.3 | 5.4 ± 4.1 | 17.3 ± 3.9 |
| 6 | 12.1 ± 2.9 | 17.2 ± 5.8 | 38.5 ± 6.1 |

Example 15

Commercial PALP Enhances Proliferation of Human Bone Marrow-Derived Mesenchymal Stem Cells in the Presence of 10% Serum Cells were split at 1:3 and then incubated for 24 hours in 10% serum-containing medium to about 30-35% confluence. Then the medium was replaced with fresh medium containing 10% serum. After about 2 hours, the cells remained either untreated or were treated with 1.5 μg/ml or 15.0 μg/ml of commercial PALP, as indicated in TABLE 9. Then the incubations were continued for 2, 4 or 6 days followed by the determination of viable cell number. The data are expressed as mean values±std. dev. of 3 determinations. The results in TABLE 9 show that on each day examined, the higher (15 μg/ml) concentration of commercial PALP enhanced the number of viable stem cells by 1.5-2.8-fold.

TABLE 9

Effects of commercial PALP on the proliferation of mesenchymal stem cells in the presence of 10% serum.

| | Cell number per culture (×10$^{-3}$) | | |
|---|---|---|---|
| Time (days) | No PALP | PALP, 1.5 μg/ml | PALP, 15 μg/ml |
| 0 | 20 | 20 | 20 |
| 2 | 4.3 ± 2.5 | 4.2 ± 2.6 | 12.2 ± 3.1 |
| 4 | 15.5 ± 2.2 | 15.1 ± 3.5 | 25.1 ± 4.3 |
| 6 | 34.9 ± 11.1 | 36.1 ± 8.8 | 53.5 ± 6.2 |

Example 16

Combined Stimulatory Effects of Fixed Concentrations of Purified PALP, Human TF and Purified Human AT on the Survival of Human Bone Marrow-Derived Mesenchymal Stem Cells in the Absence of Serum Cells were split at 1:3 and then incubated for 24 hours in 10% serum-containing medium to about 30-35% confluence. Then the medium was replaced with fresh serum-free medium. After about 2 hours, the cells remained either untreated or were treated with 10.0 μg/ml of purified PALP and/or 10.0 μg/ml of partially iron-saturated human TF and/or 150 μg/ml of purified human AT as indicated in TABLE 10. Then the incubations were continued for 2, 4 or 6 days followed by the determination of viable cell number. The data are expressed as mean values±std. dev. of 3 determinations. The results in TABLE 10 show that while both PALP and TF alone had well detectable protective effects on cell survival, the largest effect was obtained when cells were simultaneously treated with PALP, TF and AT.

TABLE 10

Combined effects of fixed concentrations PALP, TF and AT on the survival of mesenchymal stem cells in the absence of serum; a shorter-term experiment.

| | Cell number per culture (×10$^{-3}$) | | | | |
|---|---|---|---|---|---|
| Time (days) | None | PALP | TF | PALP + TF | PALP + TF + AT |
| 0 | 20 | 20 | 20 | 20 | 20 |
| 2 | 5.4 ± 2.9 | 10.1 ± 3.4 | 7.1 ± 2.6 | 12.3 ± 4.0 | 13.2 ± 3.1 |
| 4 | 4.3 ± 3.7 | 13.9 ± 4.3 | 9.2 ± 2.0 | 16.8 ± 4.6 | 21.1 ± 3.9 |
| 6 | 3.6 ± 2.2 | 14.7 ± 2.8 | 10.8 ± 1.7 | 18.9 ± 3.2 | 23.3 ± 2.1 |

Example 17

Comparison of Individual and Combined Promoting Effects of Purified PALP, Human TF and Purified Human AT with that of Commercial PALP on the Survival of Human Bone Marrow-derived Mesenchymal Stem Cells in the Absence of Serum; a Longer-Term Experiment Cells were split at 1:3 and then incubated for 24 hours in 10% serum-containing medium to about 30-35% confluence. Then the medium was replaced with fresh serum-free medium. After about 2 hours, the cells remained either untreated or were treated with various concentrations of commercial PALP, purified PALP, partially iron-saturated human TF, and purified human AT alone or in combinations as indicated in TABLE 11. Then the incubations were continued for up to 10 days followed by the determination of viable cell numbers. The data are expressed as mean values±std. dev. of 3 determinations. The results in TABLE 11 show again that both purified PALP (pPALP) and TF, particularly in combination, can reduce initial (between 0-2 days) death of stem cells, and after the second day the pPALP+TF and pPALP+TF+AT combinations promote increase in cell numbers. It is noteworthy that commercial PALP (cPALP) was somewhat less effective than the combinations of purified protein combinations. An obvious reason is that at the concentration of 15 µg/ml, commercial PALP does not contain sufficient amounts of PALP, TF and AT to exert an optimal effect. It is also important to point out that in this experiment AT added less to the combined effects of pPALP+TF than in the experiment described in Example 16 (TABLE 10). However, in this experiment only 50 µg/ml of AT was used in contrast to 150 µg/ml used in the previous experiment (TABLE 10). Clearly, AT has greater effects at 150 µg/ml than at 50 µg/ml concentration.

TABLE 11

Concentration-dependent individual and combined effects of PALP, TF and AT on the survival of mesenchymal stem cells in the absence of serum.

| Treatment | Cell number per culture ($\times 10^{-3}$) Treatment period (day) | | | | | |
|---|---|---|---|---|---|---|
| | 0 | 2 | 4 | 6 | 8 | 10 |
| None | 20 | 4.1 ± 0.8 | 4.0 ± 1.1 | 5.1 ± 2.1 | 6.1 ± 1.3 | 4.9 ± 0.9 |
| cPALP, 1.5 µg/ml | 20 | 4.3 ± 1.8 | 4.4 ± 2.2 | 5.0 ± 3.4 | 5.9 ± 2.0 | 6.0 ± 3.1 |
| cPALP, 15 µg/ml | 20 | 8.9 ± 2.2 | 9.8 ± 2.9 | 13.9 ± 3.5 | 18.5 ± 2.9 | 18.9 ± 3.8 |
| pPALP, 2.5 µg/ml | 20 | 4.1 ± 1.6 | 4.3 ± 2.1 | 4.9 ± 0.9 | 5.5 ± 1.5 | 5.8 ± 3.1 |
| pPALP, 7.5 µg/ml | 20 | 9.1 ± 2.2 | 10.1 ± 2.1 | 11.7 ± 3.2 | 12.8 ± 2.8 | 13.9 ± 3.9 |
| pPALP, 15 µg/ml | 20 | 6.7 ± 2.6 | 9.5 ± 2.4 | 10.7 ± 3.9 | 12.3 ± 3.6 | 12.9 ± 2.8 |
| TF, 2.5 µg/ml | 20 | 4.4 ± 1.6 | 4.2 ± 2.4 | 4.7 ± 2.7 | 5.8 ± 2.5 | 6.7 ± 1.8 |
| TF, 7.5 µg/ml | 20 | 8.7 ± 2.1 | 9.3 ± 2.4 | 9.9 ± 3.5 | 10.5 ± 3.7 | 10.9 ± 2.8 |
| TF, 15 µg/ml | 20 | 5.7 ± 2.5 | 9.1 ± 2.6 | 9.7 ± 3.8 | 10.2 ± 2.6 | 9.9 ± 3.1 |
| AT, 50 µg/ml | 20 | 4.2 ± 2.0 | 4.1 ± 1.6 | 4.5 ± 1.4 | 6.7 ± 3.4 | 6.8 ± 2.6 |
| AT, 100 µg/ml | 20 | 4.1 ± 1.7 | 3.9 ± 1.5 | 4.6 ± 2.8 | 6.3 ± 1.1 | 7.8 ± 3.1 |
| pPALP, 7.5 µg/ml + TF, 7.5 µg/ml | 20 | 9.1 ± 1.8 | 10.4 ± 2.5 | 14.7 ± 2.2 | 20.5 ± 4.1 | 20.1 ± 4.4 |
| pPALP, 7.5 µg/ml + TF, 7.5 µg/ml + AT, 50 µg/ml | 20 | 9.4 ± 2.0 | 11.2 ± 1.7 | 15.6 ± 3.4 | 21.3 ± 2.5 | 22.4 ± 4.2 |

Example 18

Comparison of Individual and Combined Promoting Effects of Purified PALP, Human TF and Purified Human AT with that of Commercial PALP on the Survival and Proliferation of Human Bone Marrow-derived Mesenchymal Stem Cells in the Presence of 2% Serum The experiment was performed as described in Example 17, except that the incubation medium contained 2% fetal calf serum. The results, shown in TABLE 12, indicate that commercial PALP (cPALP) as well as combinations of purified PALP (pPALP)+TF and pPALP+TF+AT similarly enhanced cell number (indicative of stimulation of cell proliferation) during the entire incubation period. pPALP and TF alone at 7.5-15 µg/ml concentrations were less effective and had stimulatory effects on cell proliferation only between days 0-6.

TABLE 12

Concentration-dependent individual and combined effects of PALP, TF and AT on the survival and proliferation of mesenchymal stem cells in the presence of 2% serum.

| Treatment | Cell number per culture ($\times 10^{-3}$) Treatment period (day) | | | | | |
|---|---|---|---|---|---|---|
| | 0 | 2 | 4 | 6 | 8 | 10 |
| None | 20 | 4.0 ± 0.0 | 4.9 ± 1.7 | 11.2 ± 3.1 | 44.3 ± 4.1 | 44.5 ± 3.9 |
| cPALP, 1.5 µg/ml | 20 | 4.2 ± 1.7 | 5.5 ± 2.2 | 14.3 ± 3.8 | 43.4 ± 5.6 | 44.8 ± 6.4 |

TABLE 12-continued

Concentration-dependent individual and combined effects of PALP, TF and AT on the survival and proliferation of mesenchymal stem cells in the presence of 2% serum.

| Treatment | Cell number per culture (×10⁻³) Treatment period (day) | | | | | |
|---|---|---|---|---|---|---|
| | 0 | 2 | 4 | 6 | 8 | 10 |
| cPALP, 15 µg/ml | 20 | 7.8 ± 2.9 | 15.6 ± 3.7 | 34.9 ± 4.6 | 57.8 ± 5.9 | 58.5 ± 7.2 |
| pPALP, 2.5 µg/ml | 20 | 4.0 ± 1.8 | 5.3 ± 2.4 | 12.5 ± 4.4 | 41.6 ± 5.2 | 43.4 ± 5.9 |
| pPALP, 7.5 µg/ml | 20 | 7.7 ± 2.8 | 14.2 ± 3.9 | 24.9 ± 4.7 | 49.5 ± 6.2 | 48.8 ± 6.2 |
| pPALP, 15 µg/ml | 20 | 6.9 ± 3.1 | 12.4 ± 3.2 | 25.6 ± 4.5 | 48.1 ± 4.3 | 47.7 ± 4.7 |
| TF, 2.5 µg/ml | 20 | 3.7 ± 2.8 | 5.1 ± 2.7 | 11.4 ± 3.4 | 39.2 ± 4.7 | 41.4 ± 5.2 |
| TF, 7.5 µg/ml | 20 | 7.1 ± 2.6 | 13.1 ± 3.5 | 21.9 ± 4.8 | 47.5 ± 5.1 | 46.6 ± 5.1 |
| TF, 15 µg/ml | 20 | 7.0 ± 3.6 | 11.2 ± 3.3 | 23.8 ± 2.5 | 48.9 ± 2.9 | 47.3 ± 6.3 |
| AT, 50 µg/ml | 20 | 4.1 ± 2.1 | 5.4 ± 3.6 | 15.1 ± 4.2 | 45.7 ± 2.8 | 47.9 ± 5.1 |
| AT, 100 µg/ml | 20 | 4.4 ± 2.8 | 4.9 ± 2.0 | 16.6 ± 3.6 | 46.8 ± 4.4 | 49.4 ± 4.7 |
| pPALP, 7.5 µg/ml + TF, 7.5 µg/ml | 20 | 9.1 ± 2.9 | 16.5 ± 3.7 | 38.8 ± 4.2 | 66.7 ± 6.8 | 65.4 ± 5.5 |
| pPALP, 7.5 µg/ml + TF, 7.5 µg/ml + AT, 50 µg/ml | 20 | 8.8 ± 2.8 | 15.6 ± 4.4 | 40.2 ± 5.3 | 68.8 ± 4.6 | 71.2 ± 3.3 |

Example 19

Comparison of Individual and Combined Promoting Effects of Purified PALP, Human TF and Purified Human AT with that of Commercial PALP on the Survival of Human Bone Marrow-derived Mesenchymal Stem Cells in the Presence of 10% Serum The experiment was performed as described in Example 17, except that the incubation medium contained 10% fetal calf serum. The results, shown in TABLE 13, indicate that commercial PALP had practically no effects on cell numbers probably because it did not contain enough PALP and TF at this concentration. In contrast, combinations of pPALP+TF and pPALP+TF+AT enhanced cell numbers between day 0 and 6, while 7.5-15 µg/ml concentrations of pPALP and TF alone had effects only between day 0 and 2. The data mean that when applied alone, pPALP and TF initially enhanced survival of cells, and when applied in combination they also enhanced cell proliferation between day 2 and 6. Overall, as expected, 10% serum was nearly optimal for the proliferation of stem cells, and it is important that PALP and TF still could exert, at least at the earlier time periods, additional effects.

TABLE 13

Concentration-dependent individual and combined effects of PALP, TF and AT on the survival and proliferation of mesenchymal stem cells in the presence of 10% serum.

| Treatment | Cell number per culture (×10⁻³) Treatment period (day) | | | | | |
|---|---|---|---|---|---|---|
| | 0 | 2 | 4 | 6 | 8 | 10 |
| None | 20 | 4.7 ± 1.8 | 14.0 ± 3.1 | 32.3 ± 4.1 | 77.9 ± 6.7 | 79.1 ± 6.8 |
| cPALP, 1.5 µg/ml | 20 | 4.4 ± 1.1 | 12.6 ± 3.1 | 33.8 ± 5.4 | 80.1 ± 7.5 | 78.4 ± 6.4 |
| cPALP, 15 µg/ml | 20 | 4.4 ± 1.2 | 12.6 ± 4.0 | 38.8 ± 6.1 | 80.1 ± 5.3 | 78.4 ± 7.1 |
| pPALP, 2.5 µg/ml | 20 | 4.4 ± 0.7 | 13.4 ± 3.1 | 32.5 ± 2.8 | 77.1 ± 8.2 | 82.3 ± 5.8 |
| pPALP, 7.5 µg/ml | 20 | 11.1 ± 2.9 | 12.6 ± 4.2 | 41.1 ± 4.4 | 77.6 ± 6.3 | 82.3 ± 6.9 |
| pPALP, 15 µg/ml | 20 | 11.7 ± 3.3 | 15.1 ± 3.7 | 39.2 ± 3.7 | 76.7 ± 7.5 | 80.1 ± 7.4 |
| TF, 2.5 µg/ml | 20 | 4.0 ± 1.3 | 12.1 ± 3.3 | 30.5 ± 4.8 | 79.8 ± 7.6 | 77.4 ± 8.2 |
| TF, 7.5 µg/ml | 20 | 11.1 ± 2.8 | 12.6 ± 4.2 | 36.2 ± 4.0 | 81.5 ± 7.4 | 80.4 ± 6.5 |
| TF, 15 µg/ml | 20 | 11.7 ± 2.9 | 15.1 ± 3.3 | 37.3 ± 4.2 | 77.7 ± 5.6 | 79.8 ± 8.0 |
| AT, 50 µg/ml | 20 | 3.9 ± 1.8 | 10.7 ± 2.8 | 35.7 ± 3.9 | 81.3 ± 7.6 | 77.5 ± 6.2 |
| AT, 100 µg/ml | 20 | 4.2 ± 1.5 | 12.2 ± 3.6 | 31.6 ± 5.1 | 82.6 ± 8.4 | 78.1 ± 6.3 |
| pPALP, 7.5 µg/ml + TF, 7.5 µg/m | 20 | 10.8 ± 2.2 | 21.5 ± 3.7 | 54.1 ± 4.6 | 81.2 ± 6.9 | 77.3 ± 8.1 |
| pPALP, 7.5 µg/ml + TF, 7.5 µg/ml + AT, 50 µg/ml | 20 | 9.8 ± 2.5 | 19.7 ± 3.7 | 59.3 ± 5.2 | 76.9 ± 6.8 | 82.3 ± 5.8 |

Example 20

Further Confirmation of Promoting Effects of Purified PALP and Human TF on the Survival of Human Bone Marrow-derived Mesenchymal Stem Cells in the Absence of Serum

The experiment was performed as described in Example 17, except that this time each protein was used only at one fixed concentration. The results, shown in TABLE 15, confirm that at the concentrations used pPALP and TF in combination are somewhat more effective than cPALP in reducing cell death between day 0 and 2 and expanding the cell population between day 2 and 10.

TABLE 15

PALP and TF in combination promotes survival of mesenchymal stem cells in the absence of serum.

| Treatment | Cell number per culture (×10⁻³) Treatment period (day) | | | | | |
|---|---|---|---|---|---|---|
| | 0 | 2 | 4 | 6 | 8 | 10 |
| None | 20 | 4.0 ± 0.6 | 3.6 ± 0.6 | 4.3 ± 1.1 | 5.2 ± 1.7 | 5.0 ± 1.1 |
| cPALP, 15 µg/ml | 20 | 8.0 ± 1.5 | 8.5 ± 1.6 | 14.0 ± 1.9 | 15.9 ± 2.6 | 17.1 ± 2.1 |
| pPALP, 7.5 µg/ml | 20 | 7.6 ± 0.7 | 8.2 ± 0.8 | 12.2 ± 1.8 | 13.8 ± 1.9 | 13.5 ± 2.1 |
| TF, 7.5 µg/ml | 20 | 6.7 ± 1.1 | 7.2 ± 1.5 | 9.4 ± 2.1 | 11.1 ± 1.9 | 9.9 ± 1.0 |
| pPALP, 7.5 µg/ml + TF, 7.5 µg/ml | 20 | 8.8 ± 0.7 | 9.6 ± 1.2 | 14.9 ± 2.1 | 18.2 ± 2.7 | 19.4 ± 3.1 |

Example 21

Confirmation of Promoting Effects of Purified PALP and Human TF on the Survival and Proliferation of Human Bone Marrow-derived Mesenchymal Stem Cells in the Presence of 2% Serum

The experiment was performed as described in Example 17, except that 2% serum was present in the medium and this time each protein was used only at one fixed concentration. The results, shown in TABLE 16, confirm that at the concentrations used pPALP and TF in combination are somewhat more effective than cPALP in reducing cell death between day 0 and 2 and expanding the cell population between day 2 and 10.

TABLE 16

PALP and TF in combination promotes survival and proliferation of mesenchymal stem cells in the presence of 2% serum.

| Treatment | Cell number per culture (×10⁻³) Treatment period (day) | | | | | |
|---|---|---|---|---|---|---|
| | 0 | 2 | 4 | 6 | 8 | 10 |
| None | 20 | 3.8 ± 0.8 | 4.5 ± 1.3 | 10.1 ± 2.9 | 41.2 ± 3.1 | 43.7 ± 3.3 |
| cPALP, 15 µg/ml | 20 | 7.1 ± 2.8 | 14.3 ± 3.3 | 31.1 ± 3.9 | 55.2 ± 4.8 | 57.5 ± 5.3 |
| pPALP, 7.5 µg/ml | 20 | 6.9 ± 0.9 | 13.2 ± 2.4 | 20.3 ± 3.9 | 44.7 ± 4.1 | 48.1 ± 4.2 |
| TF, 7.5 µg/ml | 20 | 6.8 ± 0.7 | 12.4 ± 1.5 | 17.9 ± 3.2 | 42.1 ± 4.8 | 41.6 ± 4.3 |
| pPALP, 7.5 µg/ml + TF, 7.5 µg/ml | 20 | 8.8 ± 0.6 | 15.7 ± 1.4 | 33.8 ± 3.7 | 59.4 ± 4.1 | 61.2 ± 5.3 |

Example 22

Effect of Commercial PALP on the Regeneration of Bone Marrow after Sublethal Whole Body Irradiation

Two experiments were performed to determine if commercial PALP was able to promote regeneration of partially ablated bone marrow from endogenous stem cells i.e. promote restoration of the capacity of bone marrow to produce blood cells. In both experiments, C57B1 female (10-14 weeks old) mice received sublethal (250 cGy) whole body irradiation from a $^{137}$Cesium source (day 0). The next day (about 20 hours later), one group of mice received 1.2 mg commercial PALP (cPALP; dissolved in physiological saline) intraperitoneally, and the treatment was repeated on day 3 and day 6. In another group, mice were injected only with physiological saline. The subsequent procedure has been reported in [Vas, V., Fajka-Boja, R., Ion, G. A., Dudics, V., Monostori, E. and Uher, F. (2005), "Biphasic effect of recombinant Galectin-1 on the growth and death of early hematopoietic cells," *Stem Cells*, 23, 279-287]. Briefly, bone marrow was flushed from the femurs with Iscove's modified Dulbecco's medium (Gibco BRL, Gaithersburg, Md., USA), and after standard erythrocyte lysis, nucleated cells were counted using a hemocytometer. In the first experiment (shown in TABLE 17), samples were taken on days 0, 1, 3, and 10, while in the second experiment (shown in TABLE 18), samples were taken on days 0, 1, 3, 10, and 18.

To measure the formation of the granulocyte-macrophage colony-forming units (CFU-GM), a semisolid colony-forming cell assay was used. Nucleated bone marrow cells (isolated on days as indicated above) were plated in 35-mm Petri dishes (Costar, Cambridge, Mass., USA) in Iscove's modified Dulbecco's medium supplemented with 1% methylcellulose, 30% horse serum (Gibco), 10% WEHI-3B conditioned medium as a source of growth factors, 4 mM L-glutamine, 0.25 mM a-thioglycerol (Gibco), 1% deionized bovine serum albumine (Sigma), and antibiotics (Gibco). Cells were cultured at 37° C. in 5% $CO_2$/95% air atmosphere. CFU-GM was counted on day 9. Colonies containing at least 50 cells were counted which is a generally accepted value in the literature. Each value represents the mean±st. dev. of 3 samples (derived from 3 animals).

Data in TABLE 17 and TABLE 18 show that from the 3rd day on, injected commercial PALP enhanced the number of nucleated bone marrow cells. As a consequence, in both experiments commercial PALP also increased the number of CFU-GM per femur. Overall, the experiments indicated that commercial PALP, practically a mixture of PALP, TF and AT, enhanced regeneration of bone marrow from endogenous stem cells after a sublethal reduction in the number of bone marrow cells.

TABLE 17

Commercial PALP enhances bone marrow regeneration from endogenous stem cells.

| Time* (days) | PALP treatment | Nucleated BM** cells per femur ($\times 10^{-6}$) | CFU-GM/$10^5$ nucleated BM cells | CFU-GM per femur |
|---|---|---|---|---|
| 0 | No | 14.11 ± 0.56 | 71.3 ± 4.9 | 1006 |
| 1 | No | 3.98 ± 0.53 | 47.5 ± 6.7 | 190 |
| 3 | No | 2.55 ± 0.25 | 111.9 ± 11.2 | 285 |
| 3 | Yes | 3.01 ± 0.31 | 121.5 ± 12.5 | 366 |
| 10 | No | 7.54 ± 0.66 | 58.2 ± 6.3 | 439 |
| 10 | Yes | 10.80 ± 0.71 | 66.9 ± 5.1 | 723 |

*Days after irradiation when bone marrow was harvested;
**BM is bone marrow.

TABLE 18

Commercial PALP enhances bone marrow regeneration from endogenous stem cells.

| Time* (days) | PALP treatment | Nucleated BM** cells per femur ($\times 10^{-6}$) | CFU-GM/$10^5$ nucleated BM cells | CFU-GM per femur |
|---|---|---|---|---|
| 0 | No | 13.33 ± 0.67 | 68.4 ± 3.9 | 912 |
| 1 | No | 4.07 ± 0.64 | 49.2 ± 4.1 | 200 |
| 3 | No | 2.63 ± 0.15 | 108.7 ± 9.3 | 286 |
| 3 | Yes | 2.79 ± 0.22 | 117.4 ± 10.4 | 328 |
| 6 | No | 3.43 ± 0.42 | 77.8 ± 6.4 | 267 |
| 6 | Yes | 5.07 ± 0.25 | 83.6 ± 7.9 | 424 |
| 10 | No | 8.03 ± 0.80 | 61.5 ± 5.0 | 494 |
| 10 | Yes | 10.90 ± 0.46 | 62.7 ± 4.2 | 683 |
| 18 | No | 10.90 ± 1.59 | 65.5 ± 5.3 | 714 |
| 18 | Yes | 13.30 ± 0.59 | 68.1 ± 5.8 | 906 |

*Days after irradiation when bone marrow was harvested;
**BM is bone marrow.

Example 23

Commercial PALP and Purified PALP in Combination with TF Similarly Promotes Expansion of Transplanted Bone Marrow Cells In this experiment the goal was to determine if commercial PALP (cPALP) and a combination of purified PALP (pPALP) and TF can enhance expansion of transplanted bone marrow cells after applying a lethal dose of whole body irradiation (which reduces the number of bone marrow cells by more than 90%). C57B1 female mice (10-14 weeks old) were subjected to 900 cGy whole body irradiation from a $^{137}$Cesium source which was followed within 6 hours by infusion of one million donor nucleated bone marrow cells by tail vein injection. The next day (day 1) as well as on day 3 and day 6, one group of animals received 48 mg/kg of cPALP, while another group of animals received simultaneously 16 mg/kg of pPALP plus 16 mg/kg of TF on days 1, 3 and 6. A third group of animals remained untreated during the whole course of experiment. Bone marrow cells were collected on day 0 from non-irradiated animals as well as on days 6, 14, and 28 after irradiation and bone marrow transplantation. Nucleated bone marrow cells were quantified and CFU-GM assay was performed as described in Example 22. For each group, on the indicated days bone marrow was collected from 3 animals. Each value, presented in TABLE 19, represents the mean±st. dev. of 3 samples (derived from 3 animals).

The results show that by day 14 following transplantation, the bone marrow was re-populated by almost 50% in the animals treated with either commercial PALP or the combination of purified PALP and TF. This is compared to the about 25% re-population rate observed in the untreated animals. It is important to note here that the speed by which bone marrow regains its function is important because the faster the bone marrow regeneration is the less likely that infection will lead to death. The most critical period lasts until the bone marrow regenerates to about 50% when it can provide enough leukocytes to effectively fight infection. It is also noteworthy that in animals treated with these proteins, particularly with PALP plus TF, nearly complete regeneration of bone marrow occurs by day 28. Data from another experiment (not reported here) show that without protein treatment such level of bone marrow regeneration requires about 40-45 day.

Overall the results clearly indicate that commercial PALP and the combination of purified PALP and TF are capable of enhancing bone marrow regeneration. Thus, PALP and TF may be considered to promote the success of bone marrow transplantation in humans as well. In fact, in evaluating the full impact of these data it should be emphasized that in these experiments human proteins were used which means that almost certainly there was an antibody reaction against them. Such antibody reaction, which is unlikely to occur in humans, would eventually at least partly neutralize the positive effects of PALP and TF as the experiment progresses. Accordingly, it can be fully expected that in humans much less of these proteins will be sufficient to promote bone marrow regeneration.

Another important finding was that the effects of PALP and TF lasted for a remarkably long time period. Even though the last treatments were on day 6, they still clearly had significant effects on day 28. This is partly due to the relatively long half-life time of these proteins in the circulation (5-7 days), and partly due to the fact that those cells that expanded in the first two weeks in response to the proteins remained viable.

TABLE 19

Commercial PALP and purified PALP + TF similarly enhance bone marrow regeneration from transplanted bone marrow cells.

| Time* (days) | Treatment | BM** cells per femur ($\times 10^{-6}$) | CFU-GM/$10^5$ nucleated BM cells | CFU-GM per femur |
|---|---|---|---|---|
| 0 | None | 12.80 ± 1.46 | 78.4 ± 5.7 | 1003.5 |
| 6 | None | 0.98 ± 0.88 | 34.1 ± 5.1 | 33.4 |
| 6 | cPALP | 2.45 ± 0.76 | 41.0 ± 4.4 | 100.5 |
| 6 | pPALP + TF | 2.97 ± 0.69 | 39.8 ± 3.9 | 118.2 |
| 14 | None | 3.01 ± 1.23 | 68.5 ± 7.2 | 206.2 |
| 14 | cPALP | 5.52 ± 0.87 | 76.5 ± 8.1 | 422.3 |
| 14 | pPALP + TF | 5.50 ± 0.77 | 78.2 ± 7.6 | 430.1 |
| 28 | None | 7.35 ± 0.89 | 127.4 ± 8.4 | 936.4 |
| 28 | cPALP | 10.41 ± 0.75 | 142.1 ± 11.3 | 1,479.3 |
| 28 | pPALP + TF | 11.70 ± 10.5 | 137.2 ± 10.5 | 1,605.2 |

The invention claimed is:

1. A method for stimulating proliferation and promoting survival of transplanted mesenchymal or hematopoietic stem cells and/or progenitor cells that take residency in bone marrow of a mammal needing regeneration of one or more normal tissues, the method including administering to said mammal a composition comprising placental alkaline phosphatase to stimulate proliferation and promote survival of the transplanted mesenchymal or hematopoietic cells.

2. The method of claim 1 wherein the composition further comprises transferrin and/or $\alpha_1$-antitrypsin.

3. The method of claim 1 wherein the alkaline phosphatase is a recombinant protein.

4. The method of claim 2 wherein the transferrin is a recombinant protein.

5. The method of claim 2 wherein the $\alpha_1$-antitrypsin is a recombinant protein.

6. The method of claim 1, wherein the administration of the composition is preceded by radiation treatment and/or high dose chemotherapy to destroy the mammal's bone marrow.

7. The method of claim 1, wherein the administering comprises injecting into a mammal a suspension of the composition and a physiologically acceptable carrier.

8. The method of claim 7, wherein the injection method is intravenous, intraarterial, intraperitoneal, intramuscular, intraportal, subcutaneous, intradermal, direct injection into the target tissue or involves a minipump inserted subcutaneously allowing controlled release of proteins.

9. The method of claim 1, wherein the composition is administered together with the transplanted cells.

10. The method of claim 1, wherein the composition is administered before administering the transplanted cells.

11. The method of claim 1, wherein the composition is administered after administering the transplanted cells.

12. The method of claim 1, wherein the composition is administered at regular intervals after administration of the transplanted cells.

13. The method of claim 1 wherein the placental alkaline phosphatase and, when present, $\alpha_1$-antitrypsin and/or transferrin in combination with the placental alkaline phosphatase, amounts to about 0.01-2 gram per square meter of calculated surface area for the mammal.

14. The method of claim 1 wherein the composition is administered together with a promoter of survival and proliferation of endogenous stem cells and progenitor cells.

15. The method of claim 14, wherein the promoter is selected from the group consisting of insulin, thrombopoietin, erythropoietin, an angiopoietin-like protein, insulin-like growth factor 1, granulocyte-macrophage colony-stimulating factor, or granulocyte colony-stimulating factor.

16. A method for stimulating proliferation and promoting survival of transplanted skeletal muscle myoblasts or pre-adipocyte cells in a mammal needing regeneration of skeletal muscle or adipose tissue, the method including administering to said mammal a composition comprising placental alkaline phosphatase to stimulate proliferation and promote survival of the transplanted skeletal muscle myoblasts or pre-adipocyte cells.

17. The method of claim 16 wherein the composition further comprises transferrin and/or $\alpha_1$-antitrypsin.

18. The method of claim 16 wherein the alkaline phosphatase is a recombinant protein.

19. The method of claim 16, wherein the administration of the composition is preceded by radiation treatment and/or high dose chemotherapy to destroy the mammal's bone marrow.

20. The method of claim 16, wherein the administering comprises injecting into a mammal a suspension of the composition and a physiologically acceptable carrier.

21. The method of claim 16, wherein the composition is administered together with the transplanted cells.

22. The method of claim 16 wherein the placental alkaline phosphatase and, when present, $\alpha_1$-antitrypsin and/or transferrin in combination with the placental alkaline phosphotase, amounts to about 0.01-2 gram per square meter of calculated surface area for the mammal.

23. The method of claim 16 wherein the composition is administered together with a promoter of survival and proliferation of endogenous stem cells and progenitor cells.

* * * * *